(12) United States Patent
Hain et al.

(10) Patent No.: US 10,865,406 B2
(45) Date of Patent: Dec. 15, 2020

(54) ALS INHIBITOR HERBICIDE TOLERANT BETA VULGARIS MUTANTS

(75) Inventors: Ruediger Hain, Frankfurt (DE);
Juergen Benting, Leichlingen (DE);
Guenter Donn, Hofheim (DE);
Nathalie Knittel-Ottleben, Kriftel (DE); Bernd Holtschulte, Einbeck (DE); Andreas Loock, Einbeck (DE);
Clemens Springmann, Bad Gandersheim (DE); Rudolf Jansen, Einbeck (DE)

(73) Assignees: BAYER INTELLECTUAL PROPERTY GMBH, Monheim (DE); KWS SAAT AG, Einbeck (DE)

( * ) Notice: Subject to any disclaimer, the term of this patent is extended or adjusted under 35 U.S.C. 154(b) by 0 days.

(21) Appl. No.: 13/821,969

(22) PCT Filed: Oct. 13, 2011

(86) PCT No.: PCT/EP2011/067925
§ 371 (c)(1),
(2), (4) Date: Mar. 8, 2013

(87) PCT Pub. No.: WO2012/049268
PCT Pub. Date: Apr. 19, 2012

(65) Prior Publication Data
US 2013/0247253 A1     Sep. 19, 2013

Related U.S. Application Data

(60) Provisional application No. 61/394,463, filed on Oct. 19, 2010.

(30) Foreign Application Priority Data

Oct. 15, 2010 (EP) .................................... 10187751

(51) Int. Cl.
*C12N 15/01* (2006.01)
*A01H 1/04* (2006.01)
*A01H 1/06* (2006.01)

(52) U.S. Cl.
CPC ............... *C12N 15/01* (2013.01); *A01H 1/04* (2013.01); *A01H 1/06* (2013.01)

(58) Field of Classification Search
None
See application file for complete search history.

(56) References Cited

U.S. PATENT DOCUMENTS

| | | | |
|---|---|---|---|
| 5,378,824 A | 1/1995 | Bedbrook et al. | |
| 5,859,348 A | 1/1999 | Penner et al. | |
| 7,612,255 B2 * | 11/2009 | Gressel et al. | 800/290 |
| 2004/0171027 A1 | 9/2004 | Barnes et al. | |
| 2004/0242423 A1 * | 12/2004 | Howard | A01N 41/06 504/148 |
| 2005/0208506 A1 | 9/2005 | Zhao et al. | |
| 2005/0283858 A1 | 12/2005 | Yao et al. | |

FOREIGN PATENT DOCUMENTS

| | | | |
|---|---|---|---|
| DE | 198 21 613 | 11/1999 | |
| DE | 19821613 A1 | 11/1999 | |
| WO | 96/33270 | 10/1996 | |
| WO | 9633270 A1 | 10/1996 | |
| WO | 98/02526 | 1/1998 | |
| WO | 98/02526 A1 | 1/1998 | |
| WO | 98/02527 | 1/1998 | |
| WO | 9802526 A1 | 1/1998 | |
| WO | 9802527 A1 | 1/1998 | |
| WO | WO 9802526 A1 * | 1/1998 | |
| WO | WO-9802527 A1 * | 1/1998 | A01H 1/04 |
| WO | 9957965 A1 | 11/1999 | |
| WO | 2004/062351 | 7/2004 | |
| WO | 2004062351 A2 | 7/2004 | |
| WO | 2006/094084 | 9/2006 | |
| WO | 2006094084 A2 | 9/2006 | |
| WO | 2007/005581 | 1/2007 | |
| WO | 2007005581 A2 | 1/2007 | |
| WO | WO 2007005581 A2 * | 1/2007 | |
| WO | 2008/124495 | 10/2008 | |
| WO | 2008124495 A2 | 10/2008 | |
| WO | 2009/046334 | 4/2009 | |
| WO | 2009046334 A1 | 4/2009 | |
| WO | 2010037061 A1 | 4/2010 | |
| WO | 2014/091021 A1 | 6/2014 | |

OTHER PUBLICATIONS

Stougaard et al, Herbicide Resistant Mutants of Sugar Beet (*Beta vulgaris*), Abstract in Molecular Strategies for Crop Improvement, J. of Cell. Biochem. (1990) Supplement, Apr. 16-22, p. 310, Abstract No. R249; Listed as Arntzen et al in the IDS sumbitted on Mar. 8, 2013 (Cite No. 1).*
Tan et al, Imidazolinone-tolerant crops: history, current status and future, Pest Mngmt. Sci. (2005) 61-246-257.*
Alexander Dovzhenko, PhD Thesis: "Towards plastid transformation in rapeseed (*Brassica napus* L.) and sugarbeet (*Beta vulgaris* L.)", Ludwig-Maximilians-Universitat MOnchen, Germany, 2001).*
Chang et al, Biochem J. (1998) 333:765-777.*
Saunders et al, Crop Sci. (1992) 32:1357-1360; Abstract.*
Arntzen et al; "Molecular Strategies for Crop Improvements"; Journal of Cellular Biochemistry; Wiley-Liss Inc, US; vol. 44; No. Supplement; Apr. 16, 1990; pp. 257-360.

(Continued)

*Primary Examiner* — Mykola V. Kovalenko
(74) *Attorney, Agent, or Firm* — McBee Moore & Banik IP, LLC

(57) ABSTRACT

The present invention relates to an ALS inhibitor herbicide tolerant *Beta vulgaris* plant and parts thereof comprising a mutation of an endogenous acetolactate synthase (ALS) gene, wherein the ALS gene encodes an ALS polypeptide containing an amino acid different from tryptophan at a position 569 of the ALS polypeptide.

1 Claim, No Drawings
Specification includes a Sequence Listing.

(56) References Cited

OTHER PUBLICATIONS

Tan et al.; "Herbicidal Inhibitors of Amino Acid Biosynthesis and Herbicide-Tolerant Crops"; Amino Acids; The Forum for Amino Acid and Protein Research; Springer-Verlag; VI; vol. 30; No. 2; Mar. 1, 2006; pp. 195-204.
International Search Report Based on Application No. PCT/EP2011/067925 dated Feb. 21, 2012.
Ford-Lloyd,"Genetics and Breeding of Sugar Beet", Biancardi et al., Science Publishers, Enfield (NH), USA, 2005, pp. 25-33.
Beyer et al., "Sulfonylureas in Herbicides: Chemistry, Degradation, and Mode of Action"; Marcel Dekker New York, 1988, pp. 117-189.
Pontzen, "Propoxycarbazone-sodium (BAY MKH 6561): systemic properties and basis of selectivity in wheat", Pflanz.—Nachrichten, 2002, 55, pp. 37-52.
Shaner et al., "Potent Inhibitors of Acetohydroxyacid Synthase", Plant Physiol., 1984, 76, pp. 545-546.
Shaner et al., "The Imidazolinone Herbicides, CRC Press", Boca Raton, FL, 1991.
Kleschick et al., "A New Acetolactate Synthase Inhibiting Herbicide with Multicrop Selectivity", Argic. Food Chem., 1992, 40, pp. 1083-1085.
Shimizu, "Action Mechanism of Pyrimidinyl Carboxy Herbicides", Journal of Pesticide Science, 1997, 22, pp. 245-256.
Shimizu et al., "Acetolactate Syntehase Inhibitors", Springer Verlag, Berlin, 2002, pp. 1-41.
Singh, "Plant Amino Acids", Marcel Dekker Inc., New York, New York, 1999, pp. 227-247.
Hattori et al., "An acetohydroxy acid synthase mutant reveals a single site involved in multiple herbicide resistance", (1995), Mol. Gen. Genet. 246: pp. 419-425.
Stougaard et al., "Herbicide Resistant Mutants of Sugar Beet", (1990), J. Cell Biochem., Suppl. 14E, 310—XP-001028988.
Altschul et al., "Basic Local Alignment Search Tool", (1990), Journal of Molecular Biology, 215, pp. 403-410.
Thompson et al., "CLUSTAL W: improving the sensitivity of progressive multiple sequence alignment through sequence weighting, position-specific gap penalties and weight matrix choice", (1994), Nucleic Acid Res., 22, pp. 4673-4680.
Altschul et al., "Gapped BLAST and PSI-BLAST: a new generation of protein database search programs", Nucleic Acids Research, 1997, vol. 25, No. 17, pp. 3389-3402.
Altschul, "A Protein Alignment Scoring System Sensitive at All Evolutionary Distances", Journal of Molecular Evolution 36 (1993), pp. 290-300.
Singh, "Production of a monocot-specific monoclonal antibody against acetohydroxyacid synthase and its use in the purification and characterization of the enzyme", (1991), Proc. Natl. Acad. Sci., vol. 88, pp. 4572-4576.
Singh et al., "Separation and Characterization of Two Forms of Aceto−Hydroxy Acid Synthase From Black Mexican Sweet Corn Cells", (1988), Journal of Chromatogr., 444, pp. 251-261.
Ray, "Site of Action of Chlorsulfuron", (1984), Plant Physiol., 75, pp. 827-831.
Bertrand et al., "Marker-assisted selection: an approach for precision plant breeding in the twenty-first century", (2008), Philosophical Transactions R. Soc, B., 363, pp. 557-572.

Dovzhenko, "Towards plastid transformation in rapeseed and sugarbeet", PhD Thesis, Germany 2001, (142 pgs.).
Murashige et al., "A Revised Medium for Rapid Growth and Bio Assays with Tobacco Tissue Cultures", (1962), Physiologia Plantarum, vol. 15, pp. 473-497.
Meier, "Growth stages of mono- and dicotyledonous plants", BBCH Monograph, 2 Edition, 2001, (158 pgs.).
Arntzen et al, "Molecular Strategies for crop improvement", Journal of Cellular Biochemistry, Apr. 16, 1990, pp. 257-360.
Tan et al., "Herbicidal inhibitors of amino acid biosynthesis and herbicide-tolerant crops", Amino Acids, Mar. 1, 2006, pp. 195-204.
Bayer Intellectual Property GmbH et al., International Preliminary Report received in PCT/EP2011/067925, dated Apr. 25, 2013, pp. 1-9.
Bayer CropScience AG; International Search Report and Written Opinion received in PCT/2011/067925, dated Feb. 21, 2012, pp. 1-7.
T.R. Wright et al., Cell selection and inheritance of imidazolinone resistance in sugarbeet (*Beta vulgaris*), Theor Appl Genet (1998) 96:612-620, Springer-Verlag 1998.
Tardif et al., "A mutation in the herbicide target site acetogydroxyacid synthase produces morphological and structural alterations and reduces fitness in Amaranthus powellii" New Phytologist. (2006).
Mezet et al. "Sugar Beet Micropropagation", Biotechnol & Biotechnol. Eq. 20 (2006) pp. 9-14.
Chaleff et al. "Direct selection in vitro for herbicide-resistant mutants of Nicotiana tabacum", Proc. Natl. Acad. Sci. USA, vol. 75, No. 10, pp. 5104-5107, Oct. 1978.
Walter et al. "High frequency, heat treatment-induced inactivation of the phosphinothricin resistance gene in transgenic single cell suspension cultures of Medicago sa¢iva", Mol Gen Genet (1992) 235 : 189-196.
Caseley et al. "Herbicide Resistance in Weeds and Crops", British Library (1991) pp. 337-340.
"Notice of opposition to a European patent," for EP2627183, dated Jun. 29, 2018.
Wright, et al., "In vitro and whole-plant magnitude and cross-resistance characterization of two imidazolinone-resistant sugarbeet (*Beta vulgaris*) somatic cell selections," Weed Science, (1998), vol. 46: 24-29.
Sibony, et al., "Molecular basis for multiple resistance to acetolactate synthase-inhibiting herbicides and atrazine in *Amaranthus blitoides* (prostrate pigweed)," Planta, (2003), vol. 216: 1022-1027.
Tranel, et al., "Resistance of weeds to ALS-inhibiting herbicides: what have we learned?" Weed Science, (2002), vol. 50: 700-712.
Bernasconi, et al., "A Naturally Occurring Point Mutation Confers Broad Range Tolerance to Herbicides That Target Acetolactate Synthase," J. Biol. Chem., (1995), vol. 270, No. 29: 17381-17385.
Anderson, et al., "Herbicide-tolerant mutants of corn," Genome, (1989), vol. 31: 994-999.
Swanson, et al., "Microspore mutagenesis and selection: Canola plants with field tolerance to the imidazollinones," Theor Appl Genet, (1989), vol. 78: 525-530.
Experimental Report of Dr. Bernd Laber for submission with the European Patent Office in the opposition proceedings concerning EP 2 627 183 81, dated Jun. 26, 2019.
Declaration of Dr. Rudolf Jansen for submission in the European opposition proceedings concerning EP 2 627 183 B1, dated Jun. 5, 2019.

\* cited by examiner

ALS INHIBITOR HERBICIDE TOLERANT BETA VULGARIS MUTANTS

CROSS REFERENCE TO RELATED APPLICATIONS

This application is a § 371 National Stage Application of PCT/EP2011/067925 filed Oct. 13, 2011, which claims priority to European Application No. 10187751.2 filed Oct. 15, 2010 and U.S. Provisional Application No. 61/394,463, filed Oct. 9, 2010.

BACKGROUND OF THE INVENTION

Field of the Invention

Description of Related Art

The present invention relates to ALS inhibitor herbicide tolerant *Beta vulgaris* plants and parts thereof as well as a method for their manufacture.

Cultivated forms of *Beta vulgaris* (as defined in Ford-Lloyd (2005) Sources of genetic variation, Genus Beta. In: Biancardi E, Campbell L G, Skaracis G N, De Biaggi M (eds) Genetics and Breeding of Sugar Beet. Science Publishers, Enfield (NH), USA, pp 25-33) are important agricultural crops in temperate and subtropical regions. For example, about 20% of the world sugar production is based on sugar beet. Because beet seedlings and juvenile plants during their first 6-8 weeks of their life are susceptible for strong competition caused by fast growing weeds, which outcompete the young crop plants, reliable weed control measures are imperative in these crop areas.

Since more than 40 years, herbicides are the preferred tools to control weeds in cultured beets. The products used for this purpose, like phenmedipham, desmediphan and metamitron allow to suppress the growth of weeds in beet fields without damaging the crop. Nevertheless under adverse environmental conditions the efficacy of these products leaves room for improvements, especially if noxious weeds like *Chenopodium album, Amaranthus retroflexus* and/or *Tripleurospermum inodorata* germinate over an extended period of time.

Innovative herbicidal active ingredients are highly desirable in order to improve the weed control options in beet. Such compounds should act against a broad weed spectrum, preferably from weed germination until full development of the weed plants, without affecting the beet crop irrespective of its developmental stage. Via the classical herbicide screening approach no selective herbicidal active ingredient was discovered for beet during the past decades which fulfils all these stringent properties in an agronomically superior way.

Some chemicals inhibit the enzyme "acetohydroxyacid synthase" (AHAS), also known as "acetolactate synthase" (ALS [EC 4.1.3.18]). ALS is the site of action of five structurally diverse herbicide families belonging to the class of ALS inhibitor herbicides, like (a) sulfonylurea herbicides (Beyer E. M et al. (1988), Sulfonylureas in Herbicides: Chemistry, Degradation, and Mode of Action; Marcel Dekker, New York, 1988, 117-189), (b) sulfonylaminocarbonyltriazolinone herbicides (Pontzen, R., Pflanz.-Nachrichten Bayer, 2002, 55, 37-52), (c) imidazolinone herbicides (Shaner, D. L., et al., Plant Physiol., 1984, 76, 545-546; Shaner, D. L., and O'Connor, S. L. (Eds.) The Imidazolinone Herbicides, CRC Press, Boca Raton, Fla., 1991), (d) triazolopyrimidine herbicides (Kleschick, W. A. et al., Agric. Food Chem., 1992, 40, 1083-1085), and (e) pyrimidinyl(thio)benzoate herbicides (Shimizu, T. J., Pestic. Sci., 1997, 22, 245-256; Shimizu, T. et al., Acetolactate Syntehase Inhibitors in Herbicide Classes in Development, Boger, P., Wakabayashi, K., Hirai, K., (Eds.), Springer Verlag, Berlin, 2002, 1-41).

ALS is involved in the conversion of two pyruvate molecules to an acetolactate molecule and carbon dioxide. The reaction uses thyamine pyrophosphate in order to link the two pyruvate molecules. The resulting product of this reaction, acetolactate, eventually becomes valine, leucine and isoleucine (Singh (1999) "Biosynthesis of valine, leucine and isoleucine", in Plant Amino Acids, Singh, B. K., ed., Marcel Dekker Inc. New York, N.Y., pp. 227-247).

Inhibitors of the ALS interrupt the biosynthesis of valine, leucine and isoleucine in plants. The consequence is an immediate depletion of the respective amino acid pools causing a stop of protein biosynthesis leading to a cessation of plant growth and eventually the plant dies, or—at least—is damaged.

ALS inhibitor herbicides are widely used in modern agriculture due to their effectiveness at moderate application rates and relative non-toxicity in animals. By inhibiting ALS activity, these families of herbicides prevent further growth and development of susceptible plants including many weed species. In order to provide plants with an increased tolerance to even high concentrations of ALS inhibitor herbicides that may be required for sufficient weed control, additional ALS-inhibiting herbicide-resistant breeding lines and varieties of crop plants, as well as methods and compositions for the production and use of ALS inhibiting herbicide-resistant breeding lines and varieties, are needed.

A broad variety of ALS inhibitor herbicides enable a farmer to control a wide range of weed species independently of their growth stages, but these highly efficient herbicides cannot be used in beet because conventional beet plants/commercial beet varieties are highly susceptible against these ALS inhibitor herbicides. Nevertheless, these ALS inhibitor herbicides show an excellent herbicidal activity against broadleaf and grass weed species. The first herbicides having the mode of action of inhibiting the ALS were developed for their use in agriculture already 30 years ago. Nowadays, active ingredients of this class of herbicides exhibit a strong weed control and are widely used in maize and cereals as well as in dicotyledonous crops, except beet.

The only ALS inhibitor herbicide that is known today to be applied in post-emergent application schemes in beet is Debut®. This herbicide (containing triflusulfuron-methyl as the active ingredient plus specific formulation compounds) is degraded by beets before it can inhibit the beet endogenous ALS enzyme but it has severe gaps in weed control in beet growing areas.

Since ALS inhibitor herbicides were introduced into agriculture it was observed that susceptible plant species, including naturally occurring weeds, occasionally develop spontaneous tolerance to this class of herbicides. Single base pair substitutions at specific sites of the ALS gene usually lead to more or less resistant ALS enzyme variants which show different levels of inhibition by the ALS inhibitor herbicides.

Plants conferring mutant ALS alleles therefore show different levels of tolerance to ALS inhibitor herbicides, depending on the chemical structure of the ALS inhibitor herbicide and the site of the point mutation in the ALS gene.

For example, Hattori et al. (1995), Mol. Gen. Genet. 246: 419-425, describes a single mutation in the Trp 557 codon in a *Brassica napus* cell line (according to the numbering of the *Arabidopsis thaliana* sequence that is used in the literature in order to compare all ALS/AHAS mutants this refers to position "574")-which equals position 569 of the beet ALS sequence. These authors observed resistance to several members of sub-classes of ALS inhibitor herbicides, like sulfonylureas, imidazolinones and triazolopyrimidines.

Beet mutants were described conferring a point mutation in the Ala 122 codon which led to a certain tolerance to the ALS inhibitor herbicide subclass of imidazolinones (WO 98/02526) but which is not sufficient for weed control in agricultural application schemes. No cross-tolerance to other ALS inhibitor herbicide classes were described by employing this mutant. Furthermore, beet plants conferring a second point mutation in the Pro 197 codon showed a moderate tolerance to ALS inhibitor herbicides belonging to members of the subclass of sulfonylurea herbicides. Also double mutants of these two were described (WO 98/02527). However, none of these mutants were used for the market introduction of beet varieties because the level of herbicide tolerance to ALS inhibitor herbicides was not sufficiently high in these mutants to be exploited agronomically.

Stougaard et al. (1990), J. Cell Biochem., Suppl. 14E, 310 describe the isolation of ALS mutants in a tetraploid sugar beet cell culture. Two different ALS genes (ALS I and ALS II) were isolated which differed at amino acid position 37 only. Mutant 1 contained in its ALS I gene 2 mutations, while mutant 2 contained 3 mutations in its ALS II gene. After the mutations were separated to resolve which mutation would confer resistance against an ALS inhibitor, it was revealed that ALS synthesized from a recombinant *E. coli* was herbicide resistant if it contained a point mutation in the Trp 574 codon (according to the numbering of the *Arabidopsis thaliana* sequence that is used in the literature in order to compare all ALS mutants)—which equals position 569 of the beet ALS sequence, leading to a replacement of the amino acid "Trp" by the amino acid "Leu". Stougaard et al did not show in sugar beet that the mutation at position 569 of any of the sugar beet ALS genes is sufficient in order to obtain an acceptable level of tolerance to ALS inhibitor herbicides. Moreover, Stougaard et al did not regenerate or handle sugar beet plants comprising a mutation, including Trp->Leu mutation at position 569 of sugar beet ALS.

Knowing this, Stougaard et al. constructed plant transformation vectors containing different ALS genes for use in plant transformation. However, up to now, no further data—especially not concerning the effects of the application of ALS inhibitor herbicides to plants and/or agricultural areas comprising this mutation in *Beta vulgaris* plants have been disclosed by these or other authors either in genetically engineered or mutant plants over more than 20 years, thereafter.

WO 99/57965 generally describes sulfonylurea resistant sugar beet plants and methods for obtaining them by EMS (Ethylmethanesulfonate) mutagenesis. However, apart from the research that is required to obtain such mutants, this publication does neither provide such plants, nor describes any specific location in the ALS gene that may be relevant for obtaining ALS inhibitor herbicide tolerant mutants, nor discloses any correlated agronomical use of such. Furthermore, there is a strong likelihood that—by employing such strong mutagenic compound like EMS—various further mutations may occur elsewhere in the genome and which might lead to disadvantages up to non-fertility and/or growth retardation of such obtained plants. Moreover, due to its chemical interaction with the DNA, the EMS application may have gaps of inducing specific mutations, like converting the triplet TGG into TTG, because EMS always converts a guanosine into an adenosine.

In some weed species as *Amaranthus*, the Trp 574 Leu mutation could be detected in plant populations which were repeatedly exposed to ALS inhibitor herbicides. These Trp 574 Leu mutants show a high level of tolerance to several chemical classes of ALS inhibitor herbicides, like those selected from the group consisting of sulfonylureas and sulfonylaminocarbonyltriazolinones.

WO 2008/124495 discloses ALS double and triple mutants. According to WO 2009/046334, specific mutations in the ALS gene were provided. However, agronomically exploitable herbicide tolerant *Beta vulgaris* mutants containing such mutations according to WO 2009/046334 have not been obtained so far.

Moreover, in view of the fact that, for example, sugar beet accounts for about 20% of the world sugar production, it would also be highly desirable to have available sugar beet plants which have a growth advantage versus highly potent weeds. It would thus be highly desirable to have available, with respect to the ALS gene, non-transgenic *Beta vulgaris* plants including sugar beet plants which are tolerant to ALS inhibitor herbicides. Hence, there is a need for such non-transgenic *Beta vulgaris* plants, in particular sugar beet plants which are tolerant to ALS inhibitor herbicides at an agronomically exploitable level of ALS inhibitor herbicides.

Thus, the technical problem is to comply with this need.

SUMMARY

The present invention addresses this need and thus provides as a solution to the technical problem an ALS inhibitor herbicide tolerant *Beta vulgaris* plant and parts thereof comprising a mutation of an endogenous acetolactate synthase (ALS) gene, wherein the ALS gene encodes an ALS polypeptide containing an amino acid different from tryptophan at a position 569 of the ALS polypeptide.

DETAILED DESCRIPTION OF A PREFERRED EMBODIMENT

Seeds according to present invention have been deposited with the NCIMB, Aberdeen, UK, under Number NCIMB 41705 on Mar. 12, 2010.

By applying various breeding methods, high yielding commercial varieties highly competitive in all specific markets with the add-on of a robust ALS inhibitor herbicide tolerance can be developed subsequently by using the originally obtained mutant plants.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. The word "comprise" and its variations on the one side and "contain" and its analogous variations on the other side can be used interchangeably without a preference to any of them.

In the present invention, beet plants were obtained which comprise an altered endogenous ALS gene (also referred to as "AHAS" gene), carrying a point mutation in the Trp 569 codon (in relation to the *Beta vulgaris* ALS amino acid reference sequence shown in SEQ ID NO: 2; this equals position 574 of the referenced *Arabidopsis thaliana* sequence as shown in SEQ ID NO: 6) and which point mutation was obtained by several circles of selection on specifically elected ALS inhibitor herbicides.

Due to the fact that the *B. vulgaris* plants of the present invention were obtained by isolating spontaneous mutant plant cells, which were directly regenerated to fully fertile beet plants having a point mutation as described herein in more detail. These plants are non-transgenic as far as the ALS gene is concerned.

Moreover, the plants of the present invention themselves as well as their offspring are fertile and thus useful for breeding purposes without any further manipulation that may cause stress induced further alterations of the genetic background. Such plants obtained according to the selection procedure applied herein can directly be employed in order to generate beet varieties and/or hybrids conferring agronomically useful levels of tolerance to ALS inhibitor herbicides, thus allowing innovative weed control measures in beet growing areas.

When used herein, the term "transgenic" means that a gene—which can be of the same or a different species—has been introduced via an appropriate biological carrier, like *Agrobacterium tumefaciens* or by any other physical means, like protoplast transformation or particle bombardment, into a plant and which gene is able to be expressed in the new host environment, namely the genetically modified organism (GMO).

In accordance to the before definition, the term "non-transgenic" means exactly the contrary, i.e. that no introduction of the respective gene has occurred via an appropriate biological carrier or by any other physical means. However, a mutated gene can be transferred through pollination, either naturally or via a breeding process to produce another non-transgenic plant concerning this specific gene.

An "endogenous" gene means a gene of a plant which has not been introduced into the plant by genetic engineering techniques.

The term "sequence" when used herein relates to nucleotide sequence(s), polynucleotide(s), nucleic acid sequence(s), nucleic acid(s), nucleic acid molecule, peptides, polypeptides and proteins, depending on the context in which the term "sequence" is used.

The terms "nucleotide sequence(s)", "polynucleotide(s)", "nucleic acid sequence(s)", "nucleic acid(s)", "nucleic acid molecule" are used interchangeably herein and refer to nucleotides, either ribonucleotides or deoxyribonucleotides or a combination of both, in a polymeric unbranched form of any length. Nucleic acid sequences include DNA, cDNA, genomic DNA, RNA, synthetic forms and mixed polymers, both sense and antisense strands, or may contain non-natural or derivatized nucleotide bases, as will be readily appreciated by those skilled in the art.

When used herein, the term "polypeptide" or "protein" (both terms are used interchangeably herein) means a peptide, a protein, or a polypeptide which encompasses amino acid chains of a given length, wherein the amino acid residues are linked by covalent peptide bonds. However, peptidomimetics of such proteins/polypeptides wherein amino acid(s) and/or peptide bond(s) have been replaced by functional analogs are also encompassed by the invention as well as other than the 20 gene-encoded amino acids, such as selenocysteine. Peptides, oligopeptides and proteins may be termed polypeptides. The term polypeptide also refers to, and does not exclude, modifications of the polypeptide, e.g., glycosylation, acetylation, phosphorylation and the like. Such modifications are well described in basic texts and in more detailed monographs, as well as in the research literature. The polypeptide (or protein) that is preferably meant herein is the *B. vulgaris* ALS polypeptide (or ALS protein) [SEQ ID NO: 2].

Amino acid substitutions encompass amino acid alterations in which an amino acid is replaced with a different naturally-occurring amino acid residue. Such substitutions may be classified as "conservative', in which an amino acid residue contained in the wild-type ALS protein is replaced with another naturally-occurring amino acid of similar character, for example Gly↔Ala, Val↔Ile↔Leu, Asp↔Glu, Lys↔Arg, Asn↔Gln or Phe↔Trp↔Tyr. Substitutions encompassed by the present invention may also be "non-conservative", in which an amino acid residue which is present in the wild-type ALS protein is substituted with an amino acid with different properties, such as a naturally-occurring amino acid from a different group (e.g. substituting a charged or hydrophobic amino acid with alanine. "Similar amino acids", as used herein, refers to amino acids that have similar amino acid side chains, i.e. amino acids that have polar, non-polar or practically neutral side chains. "Non-similar amino acids", as used herein, refers to amino acids that have different amino acid side chains, for example an amino acid with a polar side chain is non-similar to an amino acid with a non-polar side chain. Polar side chains usually tend to be present on the surface of a protein where they can interact with the aqueous environment found in cells ("hydrophilic" amino acids). On the other hand, "non-polar" amino acids tend to reside within the center of the protein where they can interact with similar non-polar neighbours ("hydrophobic" amino acids"). Examples of amino acids that have polar side chains are arginine, asparagine, aspartate, cysteine, glutamine, glutamate, histidine, lysine, serine, and threonine (all hydrophilic, except for cysteine which is hydrophobic). Examples of amino acids that have non-polar side chains are alanine, glycine, isoleucine, leucine, methionine, phenylalanine, proline, and tryptophan (all hydrophobic, except for glycine which is neutral).

Generally, the skilled person knows, because of his common general knowledge and the context when the terms ALS, ALSL, AHAS or AHASL are used, as to whether the nucleotide sequence or nucleic acid, or the amino acid sequence or polypeptide, respectively, is meant.

The term "gene" when used herein refers to a polymeric form of nucleotides of any length, either ribonucleotides or deoxyribonucleotides. The term includes double- and single-stranded DNA and RNA. It also includes known types of modifications, for example, methylation, "caps", substitutions of one or more of the naturally occurring nucleotides with an analog. Preferably, a gene comprises a coding sequence encoding the herein defined polypeptide. A "coding sequence" is a nucleotide sequence which is transcribed into mRNA and/or translated into a polypeptide when placed or being under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleic acid sequences or genomic DNA, while introns may be present as well under certain circumstances.

When used herein the term "*Beta vulgaris*" is abbreviated as "*B. vulgaris*". Furthermore, the term "beet" is used herein. Said three terms are interchangeably used and should be understood to fully comprise the cultivated forms of *Beta vulgaris* as defined in Ford-Lloyd (2005) Sources of genetic variation, Genus *Beta*. In: Biancardi E, Campbell L G, Skaracis G N, De Biaggi M (eds) Genetics and Breeding of Sugar Beet. Science Publishers, Enfield (NH), USA, pp 25-33. Similarly, for example, the term "*Arabidopsis thaliana*" is abbreviated as "*A. thaliana*". Both terms are interchangeably used herein.

The term "position" when used in accordance with the present invention means the position of either an amino acid within an amino acid sequence depicted herein or the position of a nucleotide within a nucleotide sequence depicted herein. The term "corresponding" as used herein also includes that a position is not only determined by the number of the preceding nucleotides/amino acids.

The position of a given nucleotide in accordance with the present invention which may be substituted may vary due to deletions or additional nucleotides elsewhere in the ALS 5'-untranslated region (UTR) including the promoter and/or any other regulatory sequences or gene (including exons and introns). Similarly, the position of a given amino acid in accordance with the present invention which may be substituted may vary due to deletion or addition of amino acids elsewhere in the ALS polypeptide.

Thus, under a "corresponding position" in accordance with the present invention it is to be understood that nucleotides/amino acids may differ in the indicated number but may still have similar neighbouring nucleotides/amino acids. Said nucleotides/amino acids which may be exchanged, deleted or added are also comprised by the term "corresponding position".

In order to determine whether a nucleotide residue or amino acid residue in a given ALS nucleotide/amino acid sequence corresponds to a certain position in the nucleotide sequence of SEQ ID NO: 1 or the amino acid sequence of SEQ ID NO: 2, the skilled person can use means and methods well-known in the art, e.g., alignments, either manually or by using computer programs such as BLAST (Altschul et al. (1990), Journal of Molecular Biology, 215, 403-410), which stands for Basic Local Alignment Search Tool or ClustalW (Thompson et al. (1994), Nucleic Acid Res., 22, 4673-4680) or any other suitable program which is suitable to generate sequence alignments.

SEQ ID NO: 1 is the nucleotide sequence encoding *Beta vulgaris* wild type ALS. SEQ ID NO: 2 is the *Beta vulgaris* amino acid sequence derived from SEQ ID NO: 1. Accordingly, the codon at position 1705-1707 of the nucleotide sequence of SEQ ID NO: 1 encodes the amino acid at position 569 (i.e. the amino acid "Trp" according to the three letter code or "W" according to the one letter code) of SEQ ID NO: 2.

In the alternative to determine whether a nucleotide residue or amino acid residue in a given ALS nucleotide/ amino acid sequence corresponds to a certain position in the nucleotide sequence of SEQ ID NO: 1, the nucleotide sequence encoding *A. thaliana* wild type ALS shown in SEQ ID NO: 5 can be used. SEQ ID NO: 6 is the *A. thaliana* amino acid sequence derived from SEQ ID NO: 5.

Accordingly, the codon at position 1720-1722 of the nucleotide sequence of SEQ ID NO: 5 encodes the amino acid at position 574 (i,e, the amino acid "Trp" according to the three letter code or "W" according to the one letter code) of SEQ ID NO. 6.

If the *A. thaliana* wild type ALS nucleotide sequence shown in SEQ ID NO: 5 is used as reference sequence (as it is done in most of the relevant literature and, therefore, is used to enable an easier comparison to such known sequences), the codon encoding an amino acid different from tryptophan is at a position corresponding to position 1720-1722 of the nucleotide sequence of the *A. thaliana* ALS gene shown in SEQ ID NO: 5.

However, SEQ ID NO: 1 is preferred as the reference nucleotide sequence and SEQ ID NO: 2 is preferred as the reference amino acid sequence in all of the subsequent disclosures.

The following table provides an overview on the reference sequences used herein when the position of the point mutation in a nucleotide sequence or the substitution in an amino acid sequence is determined:

| SEQ ID NO: | Type of Sequence | Species |
| --- | --- | --- |
| 1 | nucleotide sequence | *B. vulgaris* |
| 2 | amino acid sequence | *B. vulgaris* |
| 3 | nucleotide sequence (mutated) | *B. vulgaris* |
| 4 | amino acid sequence (mutated) | *B. vulgaris* |
| 5 | nucleotide sequence | *A. thaliana* |
| 6 | amino acid sequence | *A. thaliana* |

Thus, in any event, the equivalent position could still be determined through alignment with a reference sequence, such as SEQ ID NO: 1 or 5 (nucleotide sequence) or SEQ ID NO: 2 or 6 (amino acid sequence).

In view of the difference between the *B. vulgaris* wild-type ALS gene and the ALS gene comprised by a *B. vulgaris* plant of the present invention, the ALS gene (or polynucleotide or nucleotide sequence) comprised by a *B. vulgaris* plant of the present invention may also be regarded as a "mutant ALS gene", "mutant ALS allele", "mutant ALS polynucleotide" or the like. Thus, throughout the specification, the terms "mutant allele", "mutant ALS allele", "mutant ALS gene" or "mutant ALS polynucleotide" are used interchangeably.

Unless indicated otherwise herein, these terms refer to a nucleotide sequence that comprises a codon encoding an amino acid different from tryptophan at a position corresponding to position 1705-1707 of the nucleotide sequence of the *B. vulgaris ALS gene shown in SEQ ID NO: 1*. When set in relation to the *A. thaliana* reference sequence shown in SEQ ID NO: 5, the position of the codon is 1720-1722.

Likewise, these terms refer to a nucleotide sequence that encodes an ALS protein having at a position corresponding to position 569 of the amino acid sequence of the *Beta vulgaris* ALS protein shown in SEQ ID NO: 2 an amino acid different from tryptophan. When set in relation to the *A. thaliana* reference sequence shown in SEQ ID NO: 6, the position is 574.

An "amino acid different from tryptophan" (indicated by "Trp" in the three letter code or "W" in the equivalently used one letter code) includes any naturally-occurring amino acid different from tryptophan. These naturally-occurring amino acids include alanine (A), arginine (R), asparagine (N), aspartate (D), cysteine (C), glutamine (Q), glutamate (E), glycine (G), histidine (H), isoleucine (I), leucine (L), lysine (K), methionine (M), phenylalanine (F), proline (P), serine (S), threonine (T), tyrosine (Y) or valine (V).

However, preferably, the amino acid different from tryptophan (belonging to the group of neutral-polar amino acids) is an amino acid with physico-chemical properties different from tryptophan, i.e. belonging to any of the amino acids showing neutral-nonpolar, acidic, or basic properties. More preferably, the amino acid different from tryptophan is selected from the group consisting of alanine, glycine, isoleucine, leucine, methionine, phenylalanine, proline, valine, and arginine. Even more preferably, said amino acid is a neutral-nonpolar amino acid such as alanine, glycine, isoleucine, leucine, methionine, phenylalanine, proline or valine. Particularly preferred said amino acid is alanine, glycine, isoleucine, leucine, valine. Even more preferred is glycine and leucine. Most preferably, it is leucine.

In contrast, unless indicated otherwise, the terms "wild-type allele," "wild-type ALS allele", "wild-type ALS gene" or "wild-type ALS polynucleotide" refer to a nucleotide sequence that encodes an ALS protein that lacks the W569 substitution in relation to SEQ ID NO: 2 (or W574 substitution in relation to SEQ ID NO: 6). These terms also refer to a nucleotide sequence comprising at a position corresponding to position 1705-1707 of the nucleotide sequence of the B. vulgaris ALS gene shown in SEQ ID NO: 1, a codon encoding an amino acid different from tryptophan.

Such a "wild-type allele", "wild-type ALS allele", "wild-type ALS gene" or "wild-type ALS polynucleotide" may, or may not, comprise mutations, other than the mutation that causes the W569 substitution.

In essence, as regards the ALS gene, the only difference between a wild-type B. vulgaris plant and the B. vulgaris plant of the present invention is preferably (and specifically) that at a position as specified herein (in particular at a position corresponding to position 1705-1707 of the nucleotide sequence of the B. vulgaris ALS gene shown in SEQ ID NO: 1), the B. vulgaris plant of the present invention comprises a codon encoding an amino acid different from tryptophan, preferably the codon encodes an amino acid as specified herein elsewhere. However, as mentioned above, further differences such as additional mutations may be present between wild-type and the mutant ALS allele as specified herein. Yet, these further differences are not relevant as long as the difference explained before is present.

Consequently, the W569 substitution (or W574 substitution when the A. thaliana ALS amino acid sequence of SEQ ID NO: 6 is used as reference) is a result of an alteration of the codon at a position corresponding to position 1705-1707 of the nucleotide sequence shown in SEQ ID NO: 1 (or at a position corresponding to position 1720-1722 of the nucleotide sequence shown in SEQ ID NO: 5, respectively).

Preferably, the substitution at position 569 is a W→L substitution, wherein "L" is encoded by any of the codons "CTT", "CTC", "CTA", "CTG", "TTA" or "TTG".

Most preferably, the substitution at position 569 is a W→L substitution, because of a transversion of the "G" nucleotide at a position corresponding to position 1706 of the nucleotide sequence shown in SEQ ID NO: 1 (or at a position corresponding to position 1721 of the nucleotide sequence shown in SEQ ID NO: 5, respectively), to a "T" nucleotide. Accordingly, the codon at a position corresponding to position 1705-1707 of the nucleotide sequence shown in SEQ ID NO: 1 (or at a position corresponding to position 1720-1722 of the nucleotide sequence shown in SEQ ID NO: 5, respectively) is changed from "TGG" to "TTG". While the codon "TGG" encodes tryptophan, the codon "TTG" encodes leucine.

Hence, in the most preferred embodiment, the present invention provides a Beta vulgaris plant comprising in the nucleotide sequence of the endogenous ALS gene, the codon TTG (encoding leucine) at a position corresponding to position 1705-1707 of the nucleotide sequence of the B. vulgaris ALS mutant gene shown in SEQ ID NO: 1, said nucleotide sequence comprising (or less preferably consisting of) SEQ ID NO: 3.

The B. vulgaris plants encoding an ALS polypeptide having at a position corresponding to position 569 of the amino acid sequence of the Beta vulgaris ALS protein shown in SEQ ID NO: 2 an amino acid different from tryptophan, preferably comprise in the nucleotide sequence of the endogenous ALS gene a codon encoding an amino acid different from tryptophan at a position corresponding to position 1705-1707 of the nucleotide sequence of the B. vulgaris ALS gene shown in SEQ ID NO: 1.

The term B. vulgaris "ALS" or "AHAS" gene also includes B. vulgaris nucleotide sequences which are at least 90, 95, 97, 98, or 99% identical to the B. vulgaris ALS nucleotide sequence of SEQ ID NO: 1 or 3, wherein these 60, 70, 80, 90, 95, 97, 98, or 99% identical nucleotide sequences comprise at a position corresponding to position 1705-1707 of the nucleotide sequence of SEQ ID NO: 1 a codon encoding an amino acid different from tryptophan.

Likewise, these at least 90, 95, 97, 98, or 99% identical nucleotide sequences encode an ALS polypeptide comprising at a position corresponding to position 569 of SEQ ID NO: 2 an amino acid different from tryptophan. Said identical nucleotide sequences encode an ALS protein which retains the activity as described herein, more preferably the thus-encoded ALS polypeptide is tolerant to one or more ALS inhibitor herbicides as described herein. Said term also includes allelic variants and homologs encoding an ALS polypeptide which is preferably tolerant to one or more ALS inhibitor herbicides as described herein.

In order to determine whether a nucleic acid sequence has a certain degree of identity to the nucleotide sequences of the present invention, the skilled person can use means and methods well-known in the art, e.g., alignments, either manually or by using computer programs such as those mentioned further down below in connection with the definition of the term "hybridization" and degrees of homology.

For example, BLAST, which stands for Basic Local Alignment Search Tool (Altschul, Nucl. Acids Res. 25 (1997), 3389-3402; Altschul, J. Mol. Evol. 36 (1993), 290-300; Altschul, J. Mol. Biol. 215 (1990), 403-410), can be used to search for local sequence alignments. BLAST produces alignments of both nucleotide and amino acid sequences to determine sequence similarity. Because of the local nature of the alignments, BLAST is especially useful in determining exact matches or in identifying similar sequences. The fundamental unit of BLAST algorithm output is the High-scoring Segment Pair (HSP). An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

Analogous computer techniques using BLAST (Altschul (1997), loc. cit.; Altschul (1993), loc. cit.; Altschul (1990), loc. cit.) are used to search for identical or related molecules in nucleotide databases such as GenBank or EMBL. This analysis is much faster than multiple membrane-based hybridizations. In addition, the sensitivity of the computer search can be modified to determine whether any particular match is categorized as exact or similar. The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1-2% error; and at 70, the match will be exact. Similar molecules are usually identified by selecting those which show product scores between 15 and 40, although lower scores may identify related molecules.

The term *B. vulgaris* "ALS" or "AHAS" polypeptide also includes amino acid sequences which are at least 90, 95, 97, 98, or 99% identical to the ALS amino acid sequence of SEQ ID NO: 2 or 4, wherein these at least 90, 95, 97, 98, or 99% identical amino acid sequences comprising at a position corresponding to position 569 of SEQ ID NO: 2 an amino acid different from tryptophan. Said identical amino acid sequences retain the activity of ALS as described herein, more preferably the ALS polypeptide is tolerant to ALS inhibitor herbicides as described herein.

ALS activity, if required, can be measured in accordance with the assay described in Singh (1991), Proc. Natl. Acad. Sci. 88:4572-4576.

However, the ALS nucleotide sequences referred to herein encoding an ALS polypeptide preferably confer tolerance to one or more ALS inhibitor herbicides (or, vice versa, less sensitivity to an ALS inhibitor herbicide) as described herein. This is because of the point mutation leading to an amino acid substitution as described herein.

Accordingly, tolerance to an ALS inhibitor herbicide (or, vice versa, less sensitivity to an ALS inhibitor herbicide) can be measured by comparison of ALS activity obtained from cell extracts from plants containing the mutated ALS sequence and from plants lacking the mutated ALS sequence in the presence of an ALS-inhibitor herbicide, like it is described in Singh et al (1988) [J. Chromatogr., 444, 251-261].

However, a more preferred activity assay for the ALS polypeptide encoded by a nucleotide sequence comprising a codon encoding an amino acid different from tryptophan at a position corresponding to position 1705-1707 of the nucleotide sequence of the *B. vulgaris* ALS gene shown in SEQ ID NO: 1 can be done as follows:

The coding sequence of a *Beta vulgaris* wild-type and a mutant *B. vulgaris* plant is cloned into, for example, Novagen pET-32a(+) vectors and the vectors are transformed into, for example, *Escherichia coli* AD494 according to the instructions of the manufacturer. Bacteria are preferably grown at 37° C. in medium under selection pressure such as in LB-medium containing 100 mg/l carbenicillin and 25 mg/l kanamycin, are induced with, for example, 1 mM isopropyl-β-D-thiogalactopyranoside at an $OD_{600}$ of preferably about 0.6, cultivated for about 16 hours at preferably 18° C. and harvested by centrifugation. Bacterial pellets are resuspended in 100 mM sodium phosphate buffer pH 7.0 containing 0.1 mM thiamine-pyrophosphate, 1 mM $MgCl_2$, and 1 µM FAD at a concentration of 1 gram wet weight per 25 ml of buffer and disrupted by sonification. The crude protein extract obtained after centrifugation is used for ALS activity measurements.

ALS assays are then carried out in, for example, 96-well microtiter plates using a modification of the procedure described by Ray (1984), Plant Physiol., 75, 827-831. The reaction mixture contains preferably 20 mM potassium phosphate buffer pH 7.0, mM sodium pyruvate, 0.45 mM thiamine-pyrophosphate, 0.45 mM $MgCl_2$, 9 µM FAD, ALS enzyme and various concentrations of ALS inhibitors in a final volume of about 90 µl.

Assays are initiated by adding enzyme and terminated after preferably 75 min incubation at 30° C. by the addition of 40 µl 0.5 M $H_2SO_4$. After about 60 min at room temperature about 80 µl of a solution of 1.4% α-naphthol and 0.14% creatine in 0.7 M NaOH is added and after an additional about 45 min incubation at room temperature the absorbance is determined at 540 nm. pI50-values for inhibition of ALS were determined as described by Ray (1984)), Plant Physiol., 75, 827-831, using the XLFit Excel add-in version 4.3.1 curve fitting program of ID Business Solutions Limited, Guildford, UK.

When plants are used, ALS activity is preferably determined in cell extracts or leaf extracts of wild type and *B. vulgaris* cell extracts or leaf extracts of the obtained mutant in the presence of various concentrations of ALS-inhibitor herbicides, preferably sulfonylurea herbicides or sulfonylamino-carbonyltriazolinone herbicides, more preferably in the presence of various concentrations of the ALS inhibitor herbicide "foramsulfuron". ALS is thus preferably extracted from sugar beet leaves or sugar beet tissue cultures as described by Ray (1984) in Plant Physiol 75:827-831.

It is preferred that the *B. vulgaris* plants of the present invention are less sensitive to an ALS inhibitor, more preferably it is at least 100 times less sensitive, more preferably, 500 times, even more preferably 1000 times and most preferably less than 2000 times. Less sensitive when used herein may, vice versa, be seen as "more tolerable" or "more resistant". Similarly, "more tolerable" or "more resistant" may, vice versa, be seen as "less sensitive".

For example, the *B. vulgaris* plants of the present invention and in particular the *B. vulgaris* plant described in the appended Examples are/is at least 2000 times less sensitive to the ALS inhibitor herbicide foramsulfuron (a member of the ALS inhibitor sublclass "sulfonylurea herbicides") compared to the wild type enzyme.

Preferably, the *B. vulgaris* plants of the present invention are less sensitive to various members of ALS inhibitor herbicides, like sulfonylurea herbicides, sulfonylamino-carbonyltriazolinone herbicides, and imidazolinone herbicides. Sulfonylurea herbicides and sulfonylaminocarbonyltriazolinone herbicides against which said plants are less sensitive are preferably selected. In a particular preferred embodiment, the *B. vulgaris* plants of the present invention are less sensitive to the ALS inhibitor herbicide formasulfuron (sulfonylurea herbicide) either alone or in combination with one or more further ALS inhibitor herbicides either from the subclass of the sulfonyurea-herbicides or any other sub-class of the ALS inhibitor herbicides.

Hence, the *B. vulgaris* plants of the present invention which are preferably less sensitive to an ALS inhibitor herbicide can likewise also be characterized to be "more tolerant" to an ALS inhibitor" (i.e. an ALS inhibitor tolerant plant).

Thus, an "ALS inhibitor tolerant" plant refers to a plant, in particular a *B. vulgaris* plant that is more tolerant to at least one ALS inhibitor herbicide at a level that would normally inhibit the growth of a normal or wild-type plant, preferably the ALS inhibitor herbicide controls a normal or wild-type plant. Said normal or wild-type plant does not comprise in the nucleotide sequence of any allele of the endogenous ALS gene, a codon encoding an amino acid different from tryptophan at a position corresponding to position 1705-1707 of the nucleotide sequence of the *B. vulgaris* ALS gene shown in SEQ ID NO: 1.

Said nucleotide sequence may generally also be characterized to be an "ALS inhibitor herbicide tolerant" nucleotide sequence. By "ALS inhibitor herbicide tolerant nucleotide sequence" is intended a nucleic acid molecule comprising a nucleotide sequence comprising at least the mutation that results in a codon encoding an amino acid different from tryptophan relative to an ALS protein which does not have at a position corresponding to position 569 of the amino acid sequence of the *B. vulgaris* ALS protein shown in SEQ ID NO: 2 an amino acid different from tryptophan, wherein said at least one mutation results in the expression of a less sensitive to an ALS inhibitor herbicide ALS protein.

By "herbicide-tolerant ALS protein", it is intended that such an ALS protein displays higher ALS activity, relative to the ALS activity of a wild-type ALS protein, in the presence of at least one ALS inhibitor herbicide that is known to interfere with ALS activity and at a concentration or level of said herbicide that is known to inhibit the ALS activity of the wild-type ALS protein.

Similarly, the terms "ALS-inhibitor herbicide(s)" or simply "ALS-inhibitor(s)" are used interchangeably. As used herein, an "ALS-inhibitor herbicide" or an "ALS inhibitor" is not meant to be limited to single herbicide that interferes with the activity of the ALS enzyme. Thus, unless otherwise stated or evident from the context, an "ALS-inhibitor herbicide" or an "ALS inhibitor" can be one herbicide or a mixture of two, three, four, or more herbicides known in the art, preferably as specified herein, each of which interferes with the activity of the ALS enzyme.

Surprisingly, it was found that even the single point mutation according to the present invention confers agronomically useful and stable levels of ALS inhibitor herbicide tolerance in *B. vulgaris* plants as well as in their offsprings, particularly, if homozygocity is established. Compared to herbicide tolerant *Beta vulgaris* plants of the same genetic background in which such mutation is only heterozygously present, the herbicide tolerant *Beta vulgaris* plants which are homozygous for the mutation revealed a better agronomical level of ALS inhibitor herbicide tolerance.

Therefore, present invention relates to an ALS inhibitor herbicide tolerant *Beta vulgaris* plant having a mutation of the endogenous acetolactate synthase (ALS) gene, wherein the ALS gene encodes an ALS polypeptide containing an amino acid different from tryptophan at a position 569 of the ALS polypeptide. The respective mutation can be heterozygously present, and can preferably be the sole mutation of the ALS gene. More preferably, the respective mutation can be homozygously present, and most preferably, the respective mutation is homozygously present as the sole mutation of the endogenous ALS gene.

It could also not be expected that only one single mutation of an ALS gene in *Beta vulgaris* would be sufficient, since, for example, WO 2010/037061 teaches that double or triple mutants in the ALS gene are necessary to confer the agromically useful ALS-inhibitor herbicide tolerance.

Therefore, *B. vulgaris* plants and parts thereof which are heterozygous for the mutation are less preferred, but are still covered by the present invention and may be sufficient for certain application schemes and/or certain environment conditions. Also covered by the present invention are plants containing at least in one allele of the endogenous ALS gene, a codon encoding an amino acid different from tryptophan, preferably leucine at a position corresponding to position 1705-1707 of the nucleotide sequence of the *B. vulgaris* ALS gene shown in SEQ ID NO: 1, and containing one (in case of diploidy) or more further alleles (in case of polyploidy) having one or more further mutations in the endogenous ALS gene.

Accordingly, when used herein the term "heterozygous" or "heterozygously" means that a plant of the present invention has different alleles at a particular locus, in particular at the ALS gene locus.

"Homozygous" or "homozygously" indicates that a plant of the present invention has two copies of the same allele on different DNA strands, in particular at the ALS gene locus.

As used herein unless clearly indicated otherwise, the term "plant" intended to mean a plant at any developmental stage.

It is preferred that the *Beta vulgaris* plant of the present invention is orthoploid or anorthoploid. An orthoploid plant may preferably be haploid, diploid, tetraploid, hexaploid, octaploid, decaploid or dodecaploid, while an anorthoploid plant may preferably be triploid or pentaploid.

Parts of plants may be attached to or separate from a whole intact plant. Such parts of a plant include, but are not limited to, organs, tissues, and cells of a plant, and preferably seeds.

Accordingly, the *B. vulgaris* plant of the present invention is non-transgenic as regards an endogenous ALS gene. Of course, foreign genes can be transferred to the plant either by genetic engineering or by conventional methods such as crossing. Said genes can be genes conferring herbicide tolerances, preferably conferring herbicide tolerances different from ALS inhibitor herbicide tolerances, genes improving yield, genes improving resistances to biological organisms, and/or genes concerning content modifications.

In a further aspect, the present invention relates to a method for the manufacture of the *Beta vulgaris* plant and the parts thereof, comprising the following steps:
(a) exposing calli, preferably from sugar beet, to about $10^{-7}$ M-$10^{-9}$ M of an ALS inhibitor herbicide, preferably foramsulfuron;
(b) selecting cell colonies which can grow in the presence of up to $3\times10^{-6}$ M of an ALS inhibitor herbicide, preferably foramsulfuron [CAS RN 173159-57-4];
(c) regenerating shoots in presence of an ALS inhibitor herbicide, preferably foramsulfuron;
(d) selecting regenerated plantlets with an ALS inhibitor herbicide, preferably foramsulfuron, iodosulfuron-methyl-sodium [CAS RN 144550-36-7] and/or a mixture of both, wherein the dose of foramsulfuron is preferably equivalent to 7-70 g a.i./ha and the dose of iodosulfuron-methyl-sodium is preferably equivalent to 1-10 g a.i./ha.

In a further aspect, the regenerated plantlets obtained according to the processes (a) to (d) above, can be employed for further manufacture of *Beta vulgaris* plants by applying the following steps (e) to (m):

(e) vegetative micropropagation of individual plantlets of step (d) to rescue different positive variants by establishing a cell line (clone) of each ALS inhibitor herbicide tolerant plantlet;

(f) longterm storage of each established clone in the vegetative state;

(g) transfer of cloned plants of each clone from the long term storage into the greenhouse;

(h) vernalisation and adaptation in vernalisation chambers to induce flowering;

(i) transfer of vernalised plants to growth rooms (controlled temperature and light);

(j) select best pollen shedding plants of best flowering clones for crossing with emasculated plants of an elite but ALS inhibitor herbicide sensitive line to overcome the negative impact of somaclonal variation on the generative fertility (male and female) of plantlets of step (d);

(k) backcross to elite line until fertility is restored and finally self heterozygous plants to reach the homozygous state;

(l) produce testcrosses with an ALS inhibitor herbicide-sensitive partner and selfed seed of each backcrossed line for field evaluations;

(m) applying agronomically relevant dose rates of different ALS inhibitor herbicides to select the best performing line, preferably in its homozygous state.

The lines obtained according to above steps (a) to (m) form the basis for the development of commercial varieties following procedures known in the breeding community supported by molecular breeding techniques (like marker assisted breeding or marker assisted selection) for speeding up the processes and to secure the correct selection of plants to either obtain the mutation in its homozygous form or in case of containing one or more mutations at various locations of the ALS encoding endogenous gene to perform the correct selection of heterozygous plants that do contain at least at one of the alleles the W569 mutation according to present invention. (For review, see Bertrand C. Y. et al. (2008), Phil. Trans. R. Soc, B., 363, 557-572)

Calli are obtained by means and methods commonly known in the art, for example, as described in the appended Examples.

Seeds obtained under step (m), above, have been deposited with the NCIMB, Aberdeen, UK, under Number NCIMB 41705.

In a further aspect, the present invention relates to a method for producing an herbicide tolerant *Beta vulgaris* plant and parts thereof comprising (i) a mutation of an endogenous acetolactate synthase (ALS) gene, wherein the ALS gene encodes an ALS polypeptide containing an amino acid different from tryptophan at a position 569 of the ALS polypeptide, and (ii) an additional mutation in the endogenous ALS gene, comprising the following steps:

(a) producing an ALS inhibitor herbicide tolerant *Beta vulgaris* plant comprising a mutation of an endogenous acetolactate synthase (ALS) gene, wherein the ALS gene encodes an ALS polypeptide containing an amino acid different from tryptophan at a position 569 of the ALS polypeptide (parent A);

(b) crossing parent A with a *Beta vulgaris* plant (parent B) containing one or more further mutations in the endogenous ALS gene at positions differing from amino acid position 569;

(c) obtaining a *Beta vulgaris* progeny that is heterozygous for the ALS gene mutation of amino acid position 569 and to one or more of any further ALS gene mutations encoded by parent B;

(d) wherein the breeding process is controlled by
(i) the application of marker assisted breeding and/or microsequencing techniques, and/or
(ii) the application of agronomically relevant doses of one or more
ALS inhibitor herbicides to which the generated progeny according to step (c) are tolerant.

Accordingly, it is envisaged that the present invention also relates to *B. vulgaris* plants obtainable by the aforementioned methods of manufacture.

In a non-limiting example, sugar beet plants of the present invention were obtained by performing the following non-limiting protocol. Without being bound by theory, the same protocol may be used for obtaining *B. vulgaris* plants other than sugar beet.

Sugar beet cell cultures were initiated from seedlings of a diploid sugar beet genotype 7T9044 (as, for example, described by Alexander Dovzhenko, PhD Thesis, Title: "Towards plastid transformation in rapeseed (*Brassica napus* L.) and sugarbeet (*Beta vulgaris* L.)", Ludwig-Maximilians-Universität München, Germany, 2001). Sugar beet seeds were immersed for 60 seconds in 70% ethanol, then rinsed twice in sterile water with 0.01% detergent and then incubated for 1-4 hours in 1% NaOCl bleach. Thereafter the seeds were washed 3 times with sterile $H_2O$ and the seeds were stored in sterile water overnight at 4° C. The embryos were then isolated using forceps and scalpel.

The freshly prepared embryos were immersed in 0.5% NaOCl for 30 min and then washed 3 times in sterile water. After the last washing step they were placed on hormone free MS agar medium (Murashige and Skoog (1962), Physiol. Plantarum, 15, 473-497). Those embryos which developed into sterile seedlings were used for the initiation of regenerable sugar beet cell cultures.

Cotyledons as well as hypocotyls were cut into 2-5 mm long segments and then cultivated on agar (0.8%) solidified MS medium containing either 1 mg/l Benzylaminopurine (BAP) or 0.25 mg/l Thidiazuron (TDZ). 4 weeks later the developing shoot cultures were transferred onto fresh agar medium of the same composition and then sub-cultured in monthly intervals. The cultures were kept at 25° C. under dim light at a 12 h/12 h light/dark cycle.

After 7-10 subcultures the shoot cultures which were grown on the thidiazuron containing medium formed a distinct callus type, which was fast growing, soft and friable. The colour of this callus type was yellowish to light green. Some of these friable calli consistently produced chlorophyll containing shoot primordia from embryo-like structures. These fast growing regenerable calli were used for the selection of ALS-inhibitor herbicide tolerant sugar beet mutants.

When this callus type was exposed to $10^{-9}$ M of the sulfonylurea foramsulfuron (CAS RN 173159-57-4), the cells survived, but produced less than 50% of the biomass of their siblings on medium devoid of the inhibitor. On medium containing $3 \times 10^{-8}$ M foramsulfuron no growth was detectable. For large scale mutant selection experiments $10^{-7}$ M foramsulfuron was chosen. Surviving and growing cell colonies were numbered and transferred after 4-6 weeks onto fresh medium containing $3 \times 10^{-7}$ M of the inhibitor. One of these cell colonies was able to grow not only at this concentration of the inhibitor but even in presence of $3 \times 10^{-6}$ M of foramsulfuron. From this clone (SB574TL), shoots were regenerated in presence of the ALS-inhibitor herbicide and then the shoots were transferred to MS medium containing 0.05 mg/l Naphthalene acetic acid (NAA).

Within 4-12 weeks the shoots formed roots and then they were transferred into sterile plant containers filled with wet, sterilized perlite, watered with half strength MS inorganic ingredients. Alternatively the plantlets were transferred directly from the agar solidified medium in a perlite containing soil mixture in the greenhouse. During the first 10-15 days after transfer into soil containing substrate the plants were kept in an environment with high air humidity. During and after they were weaned to normal greenhouse air humidity regimes the plants were kept in the greenhouse under artificial light (12 h) at 20+−3° C./15+−2° C. day/night temperatures.

3-5 weeks later, the regenerated plants from the above obtained foramsulfuron tolerant cell culture (SB574TL) as well as from the wild type cell cultures were treated with foramsulfuron, iodosulfuron-methyl-sodium (CAS RN 144550-3-7) and a mixture of both active ingredients. The herbicide doses tested were equivalent to 7-70 g a.i./ha for foramsulfuron and 1-10 g a.i./ha for iodosulfuron-methyl-sodium. Regenerated plants from this tolerant cell line tolerated even the highest herbicide doses (foramsulfuron, iodosulfuron-methyl-sodium and their mixtures in the ratio 7:1 whereas even the lowest doses killed the wild type plants.

Offsprings were tested as follows (in a non-limiting way):

Based on SB574TL, F2 and F3 seeds of experimental hybrids conferring the resistance allele in the heterozygous state as well as F4-F6 seeds conferring the mutant allele in the homozygous state were sown in the field and treated with foramsulfuron, iodosulfuron-methyl-sodium as well as with mixtures of both ALS inhibitor herbicides when the plants developed 3-5 rosette leaves. The homozygous seedlings tolerated mixtures of 35 g foramsulfuron/ha+7 g iodosulfuron-methyl-sodium/ha without growth retardation or any signs of visible damage. In several cases, heterozygous lines showed signs of retarded growth and some leaf chlorosis at these rates, but they recovered within 3-5 weeks, whereas the conventional sugar beet seedlings were killed by the ALS inhibitor herbicides.

The ALS mutants were characterized as follows:

Extraction and nucleic acid sequence analysis of the obtained mutant was performed by LGC Genomics GmbH, Berlin, Germany according to amended standard protocols.

The nucleic acid sequence obtained from the sugar beet mutant SB574TL is shown in SEQ ID NO: 3. SEQ ID NO: 4 represents the corresponding amino acid sequence, whereas SEQ ID NO: 1 was obtained after sequencing the wild type sugar beet plant that was taken as the starting material. SEQ ID NO: 2 represents the corresponding amino acid sequence of the wild type sugar beet.

Comparison of all these sequences shows up that there is only the mutation at position 574 but no other change took place at any other part of this endogenous ALS gene.

```
(1)
                                                             SEQ ID No 1
ATGGCGGCTACCTTCACAAACCCAACATTTTCCCCTTCCTCAACTCCATTAACCAAAACC (1)
                                                             SEQ ID No 3
ATGGCGGCTACCTTCACAAACCCAACATTTTCCCCTTCCTCAACTCCATTAACCAAAACC

(61)
                                                             SEQ ID No 1
CTAAAATCCCAATCTTCCATCTCTTCAACCCTCCCCTTTTCCACCCCTCCCAAAACCCCA

(61)
                                                             SEQ ID No 3
CTAAAATCCCAATCTTCCATCTCTTCAACCCTCCCCTTTTCCACCCCTCCCAAAACCCCA (121)
                                                             SEQ ID No 1
ACTCCACTCTTTCACCGTCCCCTCCAAATCTCATCCTCCCAATCCCACAAATCATCCGCC (121)
                                                             SEQ ID No 3
ACTCCACTCTTTCACCGTCCCCTCCAAATCTCATCCTCCCAATCCCACAAATCATCCGCC (181)
                                                             SEQ ID No 1
ATTAAAACACAAACTCAAGCACCTTCTTCTCCAGCTATTGAAGATTCATCTTTCGTTTCT (181)
                                                             SEQ ID No 3
ATTAAAACACAAACTCAAGCACCTTCTTCTCCAGCTATTGAAGATTCATCTTTCGTTTCT (241)
                                                             SEQ ID No 1
CGATTTGGCCCTGATGAACCCAGAAAAGGGTCCGATGTCCTCGTTGAAGCTCTTGAGCGT (241)
                                                             SEQ ID No 3
CGATTTGGCCCTGATGAACCCAGAAAAGGGTCCGATGTCCTCGTTGAAGCTCTTGAGCGT (301)
                                                             SEQ ID No 1
GAAGGTGTTACCAATGTGTTTGCTTACCCTGGTGGTGCATCTATGGAAATCCACCAAGCT
```

```
(301)
                                                       SEQ ID No 3
GAAGGTGTTACCAATGTGTTTGCTTACCCTGGTGGTGCATCTATGGAAATCCACCAAGCT (361)
                                                       SEQ ID No 1
CTCACACGCTCTAAAACCATCCGCAATGTCCTCCCTCGCCATGAACAAGGCGGGGTTTTC (361)
                                                       SEQ ID No 3
CTCACACGCTCTAAAACCATCCGCAATGTCCTCCCTCGCCATGAACAAGGCGGGGTTTTC (421)
                                                       SEQ ID No 1
GCCGCCGAGGGATATGCTAGAGCTACTGGAAAGGTTGGTGTCTGCATTGCGACTTCTGGT (421)
                                                       SEQ ID No 3
GCCGCCGAGGGATATGCTAGAGCTACTGGAAAGGTTGGTGTCTGCATTGCGACTTCTGGT (481)
                                                       SEQ ID No 1
CCTGGTGCTACCAACCTCGTATCAGGTCTTGCTGACGCTCTCCTTGATTCTGTCCCTCTT (481)
                                                       SEQ ID No 3
CCTGGTGCTACCAACCTCGTATCAGGTCTTGCTGACGCTCTCCTTGATTCTGTCCCTCTT (541)
                                                       SEQ ID No 1
GTTGCCATCACTGGCCAAGTTCCACGCCGTATGATTGGCACTGATGCTTTTCAGGAGACT (541)
                                                       SEQ ID No 3
GTTGCCATCACTGGCCAAGTTCCACGCCGTATGATTGGCACTGATGCTTTTCAGGAGACT (601)
                                                       SEQ ID No 1
CCAATTGTTGAGGTGACAAGGTCTATTACTAAGCATAATTATTTAGTTTTGGATGTAGAG (601)
                                                       SEQ ID No 3
CCAATTGTTGAGGTGACAAGGTCTATTACTAAGCATAATTATTTAGTTTTGGATGTAGAG (661)
                                                       SEQ ID No 1
GATATTCCTAGAATTGTTAAGGAAGCCTTTTTTTAGCTAATTCTGGTAGGCCTGGACCT (661)
                                                       SEQ ID No 3
GATATTCCTAGAATTGTTAAGGAAGCCTTTTTTTAGCTAATTCTGGTAGGCCTGGACCT (721)
                                                       SEQ ID No 1
GTTTTGATTGATCTTCCTAAAGATATTCAGCAGCAATTGGTTGTTCCTGATTGGGATAGG (721)
                                                       SEQ ID No 3
GTTTTGATTGATCTTCCTAAAGATATTCAGCAGCAATTGGTTGTTCCTGATTGGGATAGG (781)
                                                       SEQ ID No 1
CCTTTTAAGTTGGGTGGGTATATGTCTAGGCTGCCAAAGTCCAAGTTTTCGACGAATGAG (781)
                                                       SEQ ID No 3
CCTTTTAAGTTGGGTGGGTATATGTCTAGGCTGCCAAAGTCCAAGTTTTCGACGAATGAG (841)
                                                       SEQ ID No 1
GTTGGACTTCTTGAGCAGATTGTGAGGTTGATGAGTGAGTCGAAGAAGCCTGTCTTGTAT (841)
                                                       SEQ ID No 3
GTTGGACTTCTTGAGCAGATTGTGAGGTTGATGAGTGAGTCGAAGAAGCCTGTCTTGTAT (901)
                                                       SEQ ID No 1
GTGGGAGGTGGGTGTTTGAATTCTAGTGAGGAGTTGAGGAGATTTGTTGAGTTGACAGGG
```

-continued (901)
                                                          SEQ ID No 3
GTGGGAGGTGGGTGTTTGAATTCTAGTGAGGAGTTGAGGAGATTTGTTGAGTTGACAGGG (961)
                                                          SEQ ID No 1
ATTCCGGTGGCTAGTACTTTGATGGGGTTGGGGTCTTACCCTTGTAATGATGAACTGTCT (961)
                                                          SEQ ID No 3
ATTCCGGTGGCTAGTACTTTGATGGGGTTGGGGTCTTACCCTTGTAATGATGAACTGTCT (1021)
                                                          SEQ ID No 1
CTTCATATGTTGGGGATGCACGGGACTGTTTATGCCAATTATGCGGTGGATAAGGCGGAT (1021)
                                                         (SEQ ID No 3
CTTCATATGTTGGGGATGCACGGGACTGTTTATGCCAATTATGCGGTGGATAAGGCGGAT (1081)
                                                          SEQ ID No 1
TTGTTGCTTGCTTTCGGGGTTAGGTTTGATGATCGTGTGACCGGGAAGCTCGAGGCGTTT (1081)
                                                          SEQ ID No 3
TTGTTGCTTGCTTTCGGGGTTAGGTTTGATGATCGTGTGACCGGGAAGCTCGAGGCGTTT (1141)
                                                          SEQ ID No 1
GCTAGCCGTGCTAAGATTGTGCATATTGATATTGACTCTGCTGAGATTGGGAAGAACAAG (1141)
                                                          SEQ ID No 1
GCTAGCCGTGCTAAGATTGTGCATATTGATATTGACTCTGCTGAGATTGGGAAGAACAAG (1201)
                                                          SEQ ID No 1
CAGCCCCATGTGTCCATTTGTGCTGATGTTAAATTGGCATTGCGGGGTATGAATAAGATT (1201)
                                                          SEQ ID No 3
CAGCCCCATGTGTCCATTTGTGCTGATGTTAAATTGGCATTGCGGGGTATGAATAAGATT (1261)
                                                          SEQ ID No 1
CTGGAGTCTAGAATAGGGAAGCTGAATTTGGATTTCTCCAAGTGGAGAGAAGAATTAGGT (1261)
                                                          SEQ ID No 3
CTGGAGTCTAGAATAGGGAAGCTGAATTTGGATTTCTCCAAGTGGAGAGAAGAATTAGGT (1321)
                                                          SEQ ID No 1
GAGCAGAAGAAGGAATTCCCACTGAGTTTTAAGACATTTGGGGATGCAATTCCTCCACAA (1321)
                                                          SEQ ID No 3
GAGCAGAAGAAGGAATTCCCACTGAGTTTTAAGACATTTGGGGATGCAATTCCTCCACAA (1381)
                                                          SEQ ID No 1
TATGCCATTCAGGTGCTTGATGAGTTGACCAATGGTAATGCTATTATAAGTACTGGTGTT (1381)
                                                          SEQ ID No 3
TATGCCATTCAGGTGCTTGATGAGTTGACCAATGGTAATGCTATTATAAGTACTGGTGTT (1441)
                                                          SEQ ID No 1
GGGCAGCACCAAATGTGGGCTGCGCAGCATTACAAGTACAGAAACCCTCGCCAATGGCTG (1441)
                                                          SEQ ID No 3
GGGCAGCACCAAATGTGGGCTGCGCAGCATTACAAGTACAGAAACCCTCGCCAATGGCTG (1501)
                                                          SEQ ID No 1
ACCTCTGGTGGGTTGGGGGCTATGGGGTTTGGGCTACCAGCCGCCATTGGAGCTGCAGTT -continued (1501)
SEQ ID No 3
ACCTCTGGTGGGTTGGGGGCTATGGGGTTTGGGCTACCAGCCGCCATTGGAGCTGCAGTT (1561)
SEQ ID No 1
GCTCGACCAGATGCAGTGGTTGTCGATATTGATGGGATGGCAGTTTTATTATGAATGTT (1561)
SEQ ID No 3
GCTCGACCAGATGCAGTGGTTGTCGATATTGATGGGATGGCAGTTTTATTATGAATGTT (1621)
SEQ ID No 1
CAAGAGTTGGCTACAATTAGGGTGGAAAATCTCCCAGTTAAGATAATGCTGCTAAACAAT (1621)
SEQ ID No 3
CAAGAGTTGGCTACAATTAGGGTGGAAAATCTCCCAGTTAAGATAATGCTGCTAAACAAT (1681)
SEQ ID No 1
CAACATTTAGGTATGGTTGTCCAATGGGAAGATAGGTTCTATAAAGCTAACCGGGCACAT (1681)
SEQ ID No 3
CAACATTTAGGTATGGTTGTCCAATTGGAAGATAGGTTCTATAAAGCTAACCGGGCACAT (1741)
SEQ ID No 1
ACATACCTTGGAAACCCTTCCAAATCTGCTGATATCTTCCCTGATATGCTCAAATTCGCT (1741)
SEQ ID No 3
ACATACCTTGGAAACCCTTCCAAATCTGCTGATATCTTCCCTGATATGCTCAAATTCGCT (1801)
SEQ ID No 1
GAGGCATGTGATATTCCTTCTGCCCGTGTTAGCAACGTGGCTGATTTGAGGGCCGCCATT (1801)
SEQ ID No 3
GAGGCATGTGATATTCCTTCTGCCCGTGTTAGCAACGTGGCTGATTTGAGGGCCGCCATT (1861)
SEQ ID No 1
CAAACAATGTTGGATACTCCAGGGCCGTACCTGCTCGATGTGATTGTACCGCATCAAGAG (1861)
SEQ ID No 3
CAAACAATGTTGGATACTCCAGGGCCGTACCTGCTCGATGTGATTGTACCGCATCAAGAG (1921)
SEQ ID No 1
CATGTGTTGCCTATGATTCCAAGTGGTGCCGGTTTCAAGGATACCATTACAGAGGGTGAT (1921)
SEQ ID No 3
CATGTGTTGCCTATGATTCCAAGTGGTGCCGGTTTCAAGGATACCATTACAGAGGGTGAT (1981)
SEQ ID No 1
GGAAGAACCTCTTATTGA (1981)
SEQ ID No 3
GGAAGAACCTCTTATTGA (1)
SEQ ID No. 2
MAATGTNPTFSPSSTPLTKTLKSQSSISSTLPFSTPPKTPTPLFHRPLQISSSQSHKSSA (1)
SEQ ID No. 4
MAATFTNPTFSPSSTPLTKTLKSQSSISSTLPFSTPPKTPTPLFHRPLQISSSQSHKSSA

(61)
SEQ ID No. 2
IKTQTQAPSSPAIEDSSFVSRFGPDEPRKGSDVLVEALEREGVTNVFAYPGGASMEIHQA (61)

SEQ ID No. 4
IKTQTQAPSSPAIEDSSFVSRFGPDEPRKGSDVLVEALEREGVTNVFAYPGGASMEIHQA (121)

SEQ ID No. 2
LTRSKTIRNVLPRHEQGGVFAAEGYARATGKVGVCIATSGPGATNLVSGLADALLDSVPL (121)

SEQ ID No. 4
LTRSKTIRNVLPRHEQGGVFAAEGYARATGVKGVCIATSGPGATNLVSGLADALLDSVPL (181)

SEQ ID No. 2
VAITGQVPRRMIGTDAFQETPIVEVTRSITKHNYLVLDVEDIPRIVKEAFFLANSGRPGP (181)

SEQ ID No. 4
VAITGQVPRRMIGTDAFQETPIVEVTRSITKHNYLVLDVEDIPRIVKEAFFLANSGRPGP (241)

(SEQ ID No. 2
VLIDLPKDIQQQLVVPDWDRPFKLGGYMSRLPKSKFSTNEVGLLEQIVRLMSESKKPVLY (241)

SEQ ID No. 4
VLIDLPKDIQQQLVVPDWDRPFKLGGYMSRLPKSKFSTNEVGLLEQIVRLMSESKKPVLY (301)

SEQ ID No. 2
VGGGCLNSSEELRRFVELTGIPVASTLMGLGSYPCNDELSLHMLGMHGTVYANYAVDKAD (301)

SEQ ID No. 4
VGGGCLNSSEELRRFVELTGIPVASTLMGLGSYPCNDELSLHMLGMHGTVYANYAVDKAD (361)

SEQ ID No. 2
LLLAFGVRFDDRVTGKLEAFASRAKIVHIDIDSAEIGKNKQPHVSICADVKLALRGMNKI (361)

SEQ ID No. 4
LLLAFGVRFDDRVTGKLEAFASRAKIVHIDIDSAEIGKNKQPHVSICADVKLALRGMNKI (421)

SEQ ID No. 2
LESRIGKLNLDFSKWREELGEQKKEFPLSFKTFGDAIPPQYAIQVLDELTNGNAIISTGV (421)

SEQ ID No. 4
LESRIGKLNLDFSKWREELGEQKKEFPLSFKTFGDAIPPQYAIQVLDELTNGNAIISTGV (481)

SEQ ID No. 2
GQHQMWAAQHYKYRNPRQWLTSGGLGAMGFGLPAAIGAAVARPDAVVVDIDGDGSFIMNV (481)

SEQ ID No. 4
GQHQMWAAQHYKYRNPRQWLTSGGLGAMGFGLPAAIGAAVARPDAVVVDIDGDGSFIMNV (541)

SEQ ID No. 2
QELATIRVENLPVKIMLLNNQHLGMVVQWEDRFYKANRAHTYLGNPSKSADIFPDMLKFA (541)

SEQ ID No. 4
QELATIRVENLPVKIMLLNNQHLGMVVQLEDRFYKANRAHTYLGNPSKSADIFPDMLKFA (601)

SEQ ID No. 2
EACDIPSARVSNVADLRAAIQTMLDTPGPYLLDVIVPHQEHVLPMIPSGAGFKDTITEGD (601)

SEQ ID No. 4
EACDIPSARVSNVADLRAAIQTMLDTPGPYLLDVIVPHQEHVLPMIPSGAGFKDTITEGD

-continued (661)
GRTSY-                                              SEQ ID No. 2

(661)
GRTSY-                                              SEQ ID No. 4

Yet, it is generally preferred that the *B. vulgaris* plants of the present invention and parts thereof are agronomically exploitable. "Agronomically exploitable" means that the *B. vulgaris* plants and parts thereof are useful for agronomical purposes. For example, the *B. vulgaris* plants should serve for the purpose of being useful for sugar production, bio fuel production (such as biogas, biobutanol), ethanol production, betaine and/or uridine production. The term "agronomically exploitable" when used herein also includes that the *B. vulgaris* plants of the present invention are preferably less sensitive against an ALS-inhibitor herbicide, more preferably it is at least 100 times less sensitive, more preferably, 500 times, even more preferably 1000 times and most preferably less than 2000 times. The ALS inhibitor herbicide is one or more described herein, preferably it is foramsulfuron either alone or in combination with one or more further ALS-inhibitor herbicide(s) either from the sub-class of the sulfonyurea herbicides or any other sub-class of the ALS-inhibitor herbicides, most preferably it is foramsulfuron in combination with a further sulfonylurea herbicide and/or an ALS-inhibitor of the sulfonylaminocarbonyltriazolinone herbicide sub-class.

Preferably, agronomically exploitable *B. vulgaris* plants, most preferably sugar beet plants, of the present invention are fully fertile, more preferably have wild-type fertility. Fertility is of utmost importance for a *B. vulgaris* plant of the present invention in order to be agronomically exploitable.

An example for an agronomically exploitable *B. vulgaris* plant is sugar beet. A sugar beet plant of the present invention when cultivated in an area of one hectare yields (about 80,000 to 90,000 sugar beets) should preferably serve for the production of at least 4 tons of sugar.

Alternatively, a sugar beet plant of the present invention should preferably contain a sugar content between 15-20%, preferably at least 17% so as to be agronomically exploitable. Thus, sugar beet plants that contain a sugar content between 15-20%, preferably at least 17% are a preferred embodiment of the present invention.

Plants of the present invention can be identified using any genotypic analysis method. Genotypic evaluation of the plants includes using techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), Allele-specific PCR (AS-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as "Microsatellites". Additional compositions and methods for analyzing the genotype of the plants provided herein include those methods disclosed in U.S. Publication No. 2004/0171027, U.S. Publication No. 2005/02080506, and U.S. Publication No. 2005/0283858.

Another aspect of the present invention is the use of the *Beta vulgaris* plant described herein and/or the harvestable parts or propagation material described herein for the manufacture/breeding of *Beta vulgaris* plants. Methods for the manufacture/breeding of *B. vulgaris* plants are described herein elsewhere. Such manufacture/breeding methods may be used to generate *B. vulgaris* plants of the present invention further comprising novel plant traits such as stress-resistance, like but not limited to drought, heat, cold, or salt stress and the like.

In a still further aspect, the present invention envisages the use of the herbicide tolerant *Beta vulgaris* plant described herein and/or harvestable parts or propagation material derived thereof in a screening method for the selection of ALS inhibitor herbicides.

A better understanding of the present invention and of its many advantages will be had from the following examples, offered for illustrative purposes only, and are not intended to limit the scope of the present invention in any way.

EXAMPLE 1

Mutant Isolation

Sugar beet cell cultures were initiated from seedlings of a diploid sugar beet genotype 7T9044 (as, for example, described by Alexander Dovzhenko, PhD Thesis, Title: "Towards plastid transformation in rapeseed (*Brassica napus* L.) and sugarbeet (*Beta vulgaris* L.)", Ludwig-Maximilians-Universität München, Germany, 2001).

Sugar beet seeds were immersed for 60 seconds in 70% ethanol, then rinsed twice in sterile water with 0.01% detergent and then incubated for 1-4 hours in 1% NaOCl bleach. Thereafter the seeds were washed 3 times with sterile $H_2O$ and the seeds were stored in sterile $H_2O$ overnight at 4° C. The embryos were then isolated using forceps and scalpel.

The freshly prepared embryos were immersed in 0.5% NaOCl for 30 min and then washed 3 times in sterile $H_2O$. After the last washing step they were placed on hormone free MS agar medium (Murashige and Skoog (1962), Physiol. Plantarum, 15, 473-497). Those embryos which developed into sterile seedlings were used for the initiation of regenerable sugar beet cell cultures.

Cotyledons as well as hypocotyls were cut into 2-5 mm long segments and then cultivated on agar (0.8%) solidified MS agar medium containing either 1 mg/l Benzylaminopurin (BAP) or 0.25 mg/l Thidiazuron (TDZ). 4 weeks later the developing shoot cultures were transferred onto fresh MS agar medium of the same composition and then sub-cultured in monthly intervals. The cultures were kept at 25° C. under dim light at a 12 h/12 h light/dark cycle.

After 7-10 days, subcultures the shoot cultures which were grown on the thidiazuron containing medium formed a distinct callus type, which was fast growing, soft and friable. The colour of this callus type was yellowish to light green. Some of these friable calli consistently produced chlorophyll containing shoot primordia from embryo-like structures. These fast growing regenerable calli were used for the selection of ALS inhibitor herbicide tolerant sugar beet mutants.

When this callus type was exposed to $10^{-9}$ M of the ALS inhibitor herbicide foramsulfuron (belonging to the sulfonylurea subclass, see above), the cells survived, but produced less than 50% of the biomass of their siblings on medium devoid of the inhibitor. On medium containing $3\times10^{-8}$ M foramsulfuron no growth was detectable. For large scale mutant selection experiments, $10^{-7}$ M foramsulfuron was chosen. Surviving and growing cell colonies were numbered and transferred after 4-6 weeks onto fresh medium containing $3\times10^{-7}$ M of the inhibitor. One of these cell colonies was able to grow not only at this concentration of the inhibitor but even in presence of $3\times10^{-6}$ M of foramsulfuron.

From this clone (SB574TL), shoots were regenerated in presence of the ALS inhibitor herbicide, and then the shoots were transferred to MS medium containing 0.05 mg/l naphthalene acetic acid (NAA).

Within 4-12 weeks the shoots formed roots and then they were transferred into sterile plant containers filled with wet, sterilized perlite, watered with half strength MS inorganic ingredients. Alternatively the plantlets were transferred directly from the agar solidified medium in a perlite containing soil mixture in the greenhouse. During the first 10-15 days after transfer into soil containing substrate the plants were kept in an environment with high air humidity. During and after they were weaned to normal greenhouse air humidity regimes the plants were kept in the greenhouse under artificial light (12 h) at 20+−3° C./15+−2° C. day/night temperatures.

3-5 weeks later, the regenerated plants from the above obtained foramsulfuron tolerant cell culture (SB574TL) as well as from the wild type cell cultures were treated with foramsulfuron, iodosulfuron-methyl-sodium (CAS RN 144550-3-7) and a mixture of both active ingredients. The herbicide doses tested were equivalent to 7-70 g a.i./ha for foramsulfuron and 1-10 g a.i./ha for iodosulfuron-methyl-sodium. Regenerated plants from this tolerant cell line tolerated even the highest herbicide doses (foramsulfuron, iodosulfuron-methyl-sodium and their mixtures in the ratio 7:1 whereas even the lowest doses killed the wild type plants.

EXAMPLE 2

Test of Offsprings

Based on SB574TL, F2 and F3 seeds of experimental hybrids conferring the resistance allele in the heterozygous state as well as F4-F6 seeds conferring the mutant allele in the homozygous state were sown in the field and treated with foramsulfuron, iodosulfuron-methyl-sodium as well as with mixtures of both ALS inhibitor herbicides when the plants developed 3-5 rosette leaves. The homozygous seedlings tolerated mixtures of 35 g foramsulfuron/ha+7 g iodosulfuron-methyl-sodium/ha without growth retardation or any signs of visible damage. Heterozygous lines showed signs of retarded growth and some leaf chlorosis at these rates, but they recovered within 3-5 weeks, whereas the conventional sugar beet seedlings were killed by the ALS inhibitor herbicides.

EXAMPLE 3

Molecular Characterization of the Obtained Sugar Beet Mutant (SB574TL)

Extraction and nucleic acid sequence analysis of the obtained mutant was performed by LGC Genomics GmbH, Berlin, Germany according to amended standard protocols.

The nucleic acid sequence obtained from the sugar beet mutant SB574TL is shown under SEQ ID NO: 3 with SEQ ID NO: 4 representing the corresponding amino acid sequence, whereas SEQ ID NO: 1 was obtained after sequencing the wild type sugar beet plant that was taken as the starting material. SEQ ID NO: 2 represents the corresponding amino acid sequence of the wild type sugar beet.

Comparison of all these sequences clearly show up that there is only one mutation at position 569 but no other change took place at any other part of this endogenous ALS gene of this sugar beet plant material.

EXAMPLE 4

Enzyme Activity Measurements

The coding sequences of *Beta vulgaris* wild-type and W574L-mutant (SB574TL) ALS gene were cloned into Novagen pET-32a(+) vectors and the vectors transformed into *Escherichia coli* AD494 according to the instructions of the manufacturer. Bacteria were grown at 37° C. in LB-medium (Luria-Broth-medium) containing 100 mg/l carbenicillin and 25 mg/l kanamycin, induced with 1 mM isopropyl-b-D-thiogalactopyranoside at an $OD_{600}$ of 0.6, cultivated for 16 hours at 18° C. and harvested by centrifugation. Bacterial pellets were resuspended in 100 mM sodium phosphate buffer pH 7.0 containing 0.1 mM thiamine-pyrophosphate, 1 mM $MgCl_2$, and 1 µM FAD at a concentration of 1 gram wet weight per 25 ml of buffer and disrupted by sonification. The crude protein extract obtained after centrifugation was used for ALS activity measurements.

ALS assays were carried out in 96-well microtiter plates using a modification of the procedure described by Ray (1984). The reaction mixture contained 20 mM potassium phosphate buffer pH 7.0, 20 mM sodium pyruvate, 0.45 mM thiamine-pyrophosphate, 0.45 mM $MgCl_2$, 9 µM FAD, ALS enzyme and various concentrations of ALS inhibitors in a final volume of 90 µl. Assays were initiated by adding enzyme and terminated after 75 min incubation at 30° C. by the addition of 40 µl 0.5 M $H_2SO_4$. After 60 min at room temperature 80 µl of a solution of 1.4% a-naphtol and 0.14% creatine in 0.7 M NaOH was added and after an additional 45 min incubation at room temperature the absorbance was determined at 540 nm. pI50-values for inhibition of ALS were determined as described by Ray (1984), using the XLFit Excel add-in version 4.3.1 curve fitting program of ID Business Solutions Limited.

In total, the mutant enzyme was at least 2000 times less sensitive against the ALS inhibitor foramsulfuron than the wild type enzyme.

EXAMPLE 5

Enzyme Activity Measurements (from Plants)

ALS was extracted from sugar beet leaves or sugar beet tissue cultures as described by Ray (1984), Plant Physiol 75:827-831.

ALS activity was determined in leaf extracts of wild type and sugar beets and leaf extracts of the obtained SB574TL in presence of various concentrations of foramsulfuron as described in Example 4.

In total, the mutant enzyme was at least 2000 times less sensitive against the ALS inhibitor foramsulfuron than the wild type enzyme.

EXAMPLE 6

Field Trials by Employing Homozygous ALS Inhibitor Herbicide Tolerant Sugar Beet Plants Based on SB574TL, F4-F6 seeds conferring the mutant allele of the endogenous ALS gene in the homozygous state were applied for further testing Plant seeds of the homozygous SB574TL mutant plants and those of the traditional variety KLARINA (commonly available ALS inhibitor sensitive reference sugar beet varieties, not having the respective mutation at position 569 in its ALS protein.) were sown in the field and grew up to various growth stages according to the BBCH standard (as defined in the monographie "Entwicklungsstadien mono- und dikotyler Pflanzen", 2nd edition, 2001, ed. Uwe Meier, Biologische Bundesanstalt für Land und Forstwirtschaft).

Afterwards the plants were treated with the respective ALS inhibitor herbicides as specified in Tables 1 below and which identical to those being employed during the selection procedure.

The water quantity applied in the various applications equaled 200 l/ha.

At 8, 14, and 28 days (as indicated in Table 1) after application (DAA) of the respective ALS inhibitor herbicide(s), the damages (phytotoxicity/phyto) on the different sugar beet plants were scored according to the scale from 0% to 100%.

In this context, "0%" means "no phytotoxicity/phyto" and "100%" means plants were completely killed.

TABLE 1

| Variety characteristic | | KLARINA | SB574TL based sugar beet | KLARINA | SB574TL based sugar beet | KLARINA | SB574TL based sugar beet |
|---|---|---|---|---|---|---|---|
| Stage of application | | BBCH 14 | BBCH 14 | BBCH 14 | BBCH 14 | BBCH 14 | BBCH 14 |
| Rating | | % phyto | % phyto | % phyto | % phyto | % phyto | % phyto |
| Application-Assessment interval | | 8 days | 8 days | 14 days | 14 days | 28 days | 28 days |
| Active substance | gai/ha | | | | | | |
| Foramsulfuron | 25 g/ha | 85 | 0 | 83 | 0 | 86 | 0 |
| Foramsulfuron | 50 g/ha | 90 | 0 | 92 | 0 | 94 | 0 |
| Iodosulfuron-methyl-sodium | 7 g/ha | 90 | 0 | 97 | 0 | 100 | 0 |

The invention claimed is:

1. A method for manufacturing an ALS inhibitor herbicide tolerant *Beta vulgaris* plant or parts thereof, comprising:
   (a) exposing calli from *B. vulgaris*, to about $10^{-7}$ M–$10^{-9}$ M of foramsulfuron;
   (b) selecting callus tissue from said calli, wherein said callus tissue can grow in the presence of up to $3\times10^{-6}$ M foramsulfuron;
   (c) regenerating shoots from said callus tissue in presence of foramsulfuron;
   (d) regenerating plantlets from said shoots;
   (e) selecting the regenerated plantlets with foramsulfuron, iodosulfuron-methyl-sodium and/or a mixture of both, wherein the plantlets comprise a mutation at a position corresponding to nucleotides 1705-1707 of the endogenous acetolactate synthase (ALS) gene shown in reference sequence SEQ ID NO: 1, wherein the mutated ALS gene encodes an ALS polypeptide containing leucine at position 569 of the ALS polypeptide shown in reference amino acid sequence SEQ ID NO: 2, and wherein the plantlets are homozygous for the mutation of the endogenous ALS gene.

* * * * *

SEQUENCE LISTING

```
<160> NUMBER OF SEQ ID NOS: 6

<210> SEQ ID NO 1
<211> LENGTH: 1998
<212> TYPE: DNA
<213> ORGANISM: Beta vulgaris

<400> SEQUENCE: 1
atggcggcta ccttcacaaa cccaacattt tcccttcct caactccatt aaccaaaacc      60
ctaaaatccc aatcttccat ctcttcaacc ctcccctttt ccaccctcc caaaaccca     120 actccactct ttcaccgtcc cctccaaatc tcatcctccc aatcccacaa atcatccgcc     180
attaaaacac aaactcaagc accttcttct ccagctattg aagattcatc tttcgtttct     240
cgatttggcc ctgatgaacc cagaaaaggg tccgatgtcc tcgttgaagc tctttgagcgt     300 gaaggtgtta ccaatgtgtt tgcttaccct ggtggtgcat ctatggaaat ccaccaagct     360
ctcacacgct ctaaaaccat ccgcaatgtc ctccctcgcc atgaacaagg cggggttttc     420
gccgccgagg gatatgctag agctactgga aaggttggtg tctgcattgc gacttctggt     480
cctggtgcta ccaacctcgt atcaggtctt gctgacgctc tccttgattc tgtccctctt     540
gttgccatca ctggccaagt tccacgccgt atgattggca ctgatgcttt tcaggagact     600
ccaattgtta aggtgacaag gtctattact aagcataatt atttagtttt ggatgtagag     660
gatattccta gaattgttaa ggaagccttt ttttagcta attctggtag gcctggacct     720
gttttgattg atcttcctaa agatattcag cagcaattgg ttgttcctga ttgggatagg     780 cctttttaagt tgggtgggta tatgtctagg ctgccaaagt ccaagttttc gacgaatgag     840
```

-continued

```
gttggacttc ttgagcagat tgtgaggttg atgagtgagt cgaagaagcc tgtcttgtat      900
gtgggaggtg ggtgtttgaa ttctagtgag gagttgagga gatttgttga gttgacaggg      960
attccggtgg ctagtacttt gatggggttg gggtcttacc cttgtaatga tgaactgtct     1020
cttcatatgt tggggatgca cgggactgtt tatgccaatt atgcggtgga taaggcggat     1080
ttgttgcttg ctttcggggt taggtttgat gatcgtgtga ccgggaagct cgaggcgttt     1140
gctagccgtg ctaagattgt gcatattgat attgactctg ctgagattgg gaagaacaag     1200
cagccccatg tgtccatttg tgctgatgtt aaattggcat tgcggggtat gaataagatt     1260
ctggagtcta gaatagggaa gctgaatttg gatttctcca agtggagaga agaattaggt     1320
gagcagaaga aggaattccc actgagtttt aagacatttg gggatgcaat tcctccacaa     1380
tatgccattc aggtgcttga tgagttgacc aatggtaatg ctattataag tactggtgtt     1440
gggcagcacc aaatgtgggc tgcgcagcat tacaagtaca gaaaccctcg ccaatggctg     1500
acctctggtg ggtgggggc tatggggttt gggctaccag ccgccattgg agctgcagtt     1560
gctcgaccag atgcagtggt tgtcgatatt gatggggatg cagtttat tatgaatgtt       1620
caagagttgg ctacaattag ggtggaaaat ctcccagtta agataatgct gctaaacaat     1680
caacatttag gtatggttgt ccaatgggaa gataggttct ataaagctaa ccgggcacat     1740
acataccttg gaaacccttc caaatctgct gatatcttcc ctgatatgct caaattcgct     1800
gaggcatgtg atattccttc tgcccgtgtt agcaacgtgg ctgatttgag ggccgccatt     1860
caaacaatgt tggatactcc agggccgtac ctgctcgatg tgattgtacc gcatcaagag     1920
catgtgttgc ctatgattcc aagtggtgcc ggtttcaagg ataccattac agagggtgat     1980
ggaagaacct cttattga                                                    1998
```

<210> SEQ ID NO 2
<211> LENGTH: 665
<212> TYPE: PRT
<213> ORGANISM: Beta vulgaris

<400> SEQUENCE: 2

```
Met Ala Ala Thr Phe Thr Asn Pro Thr Phe Ser Pro Ser Ser Thr Pro
1               5                   10                  15

Leu Thr Lys Thr Leu Lys Ser Gln Ser Ser Ile Ser Ser Thr Leu Pro
            20                  25                  30

Phe Ser Thr Pro Pro Lys Thr Pro Thr Pro Leu Phe His Arg Pro Leu
        35                  40                  45

Gln Ile Ser Ser Ser Gln Ser His Lys Ser Ser Ala Ile Lys Thr Gln
    50                  55                  60

Thr Gln Ala Pro Ser Ser Pro Ala Ile Glu Asp Ser Ser Phe Val Ser
65                  70                  75                  80

Arg Phe Gly Pro Asp Glu Pro Arg Lys Gly Ser Asp Val Leu Val Glu
                85                  90                  95

Ala Leu Glu Arg Glu Gly Val Thr Asn Val Phe Ala Tyr Pro Gly Gly
            100                 105                 110

Ala Ser Met Glu Ile His Gln Ala Leu Thr Arg Ser Lys Thr Ile Arg
        115                 120                 125

Asn Val Leu Pro Arg His Glu Gln Gly Gly Val Phe Ala Ala Glu Gly
    130                 135                 140

Tyr Ala Arg Ala Thr Gly Lys Val Gly Val Cys Ile Ala Thr Ser Gly
145                 150                 155                 160

Pro Gly Ala Thr Asn Leu Val Ser Gly Leu Ala Asp Ala Leu Leu Asp
```

-continued

```
                165                 170                 175
Ser Val Pro Leu Val Ala Ile Thr Gly Gln Val Pro Arg Arg Met Ile
                180                 185                 190
Gly Thr Asp Ala Phe Gln Glu Thr Pro Ile Val Glu Val Thr Arg Ser
                195                 200                 205
Ile Thr Lys His Asn Tyr Leu Val Leu Asp Val Glu Asp Ile Pro Arg
            210                 215                 220
Ile Val Lys Glu Ala Phe Phe Leu Ala Asn Ser Gly Arg Pro Gly Pro
225                 230                 235                 240
Val Leu Ile Asp Leu Pro Lys Asp Ile Gln Gln Gln Leu Val Val Pro
                245                 250                 255
Asp Trp Asp Arg Pro Phe Lys Leu Gly Gly Tyr Met Ser Arg Leu Pro
                260                 265                 270
Lys Ser Lys Phe Ser Thr Asn Glu Val Gly Leu Leu Glu Gln Ile Val
                275                 280                 285
Arg Leu Met Ser Glu Ser Lys Lys Pro Val Leu Tyr Val Gly Gly Gly
                290                 295                 300
Cys Leu Asn Ser Ser Glu Glu Leu Arg Arg Phe Val Glu Leu Thr Gly
305                 310                 315                 320
Ile Pro Val Ala Ser Thr Leu Met Gly Leu Gly Ser Tyr Pro Cys Asn
                325                 330                 335
Asp Glu Leu Ser Leu His Met Leu Gly Met His Gly Thr Val Tyr Ala
                340                 345                 350
Asn Tyr Ala Val Asp Lys Ala Asp Leu Leu Leu Ala Phe Gly Val Arg
                355                 360                 365
Phe Asp Asp Arg Val Thr Gly Lys Leu Glu Ala Phe Ala Ser Arg Ala
                370                 375                 380
Lys Ile Val His Ile Asp Ile Asp Ser Ala Glu Ile Gly Lys Asn Lys
385                 390                 395                 400
Gln Pro His Val Ser Ile Cys Ala Asp Val Lys Leu Ala Leu Arg Gly
                405                 410                 415
Met Asn Lys Ile Leu Glu Ser Arg Ile Gly Lys Leu Asn Leu Asp Phe
                420                 425                 430
Ser Lys Trp Arg Glu Glu Leu Gly Glu Gln Lys Lys Glu Phe Pro Leu
                435                 440                 445
Ser Phe Lys Thr Phe Gly Asp Ala Ile Pro Pro Gln Tyr Ala Ile Gln
                450                 455                 460
Val Leu Asp Glu Leu Thr Asn Gly Asn Ala Ile Ile Ser Thr Gly Val
465                 470                 475                 480
Gly Gln His Gln Met Trp Ala Ala Gln His Tyr Lys Tyr Arg Asn Pro
                485                 490                 495
Arg Gln Trp Leu Thr Ser Gly Gly Leu Gly Ala Met Gly Phe Gly Leu
                500                 505                 510
Pro Ala Ala Ile Gly Ala Ala Val Ala Arg Pro Asp Ala Val Val Val
                515                 520                 525
Asp Ile Asp Gly Asp Gly Ser Phe Ile Met Asn Val Gln Glu Leu Ala
                530                 535                 540
Thr Ile Arg Val Glu Asn Leu Pro Val Lys Ile Met Leu Leu Asn Asn
545                 550                 555                 560
Gln His Leu Gly Met Val Val Gln Trp Glu Asp Arg Phe Tyr Lys Ala
                565                 570                 575
Asn Arg Ala His Thr Tyr Leu Gly Asn Pro Ser Lys Ser Ala Asp Ile
                580                 585                 590
```

```
Phe Pro Asp Met Leu Lys Phe Ala Glu Ala Cys Asp Ile Pro Ser Ala
            595                 600                 605

Arg Val Ser Asn Val Ala Asp Leu Arg Ala Ala Ile Gln Thr Met Leu
        610                 615                 620

Asp Thr Pro Gly Pro Tyr Leu Leu Asp Val Ile Val Pro His Gln Glu
625                 630                 635                 640

His Val Leu Pro Met Ile Pro Ser Gly Ala Gly Phe Lys Asp Thr Ile
                645                 650                 655

Thr Glu Gly Asp Gly Arg Thr Ser Tyr
            660                 665

<210> SEQ ID NO 3
<211> LENGTH: 1998
<212> TYPE: DNA
<213> ORGANISM: Beta vulgaris
<220> FEATURE:
<221> NAME/KEY: mutation
<222> LOCATION: (1706)..(1706)
<223> OTHER INFORMATION: Substitution of a Guanosine by a Thymidine

<400> SEQUENCE: 3
atggcggcta ccttcacaaa cccaacattt tccccttcct caactccatt aaccaaaacc     60
ctaaaatccc aatcttccat ctcttcaacc ctcccctttt ccaccccctc caaaaccccca    120 actccactct ttcaccgtcc cctccaaatc tcatcctccc aatcccacaa atcatccgcc    180
attaaaacac aaactcaagc accttcttct ccagctattg aagattcatc tttcgtttct    240
cgatttggcc ctgatgaacc agaaaaaggg tccgatgtcc tcgttgaagc tcttgagcgt    300
gaaggtgtta ccaatgtgtt tgcttaccct ggtggtgcat ctatggaaat ccaccaagct    360
ctcacacgct ctaaaaccat ccgcaatgtc ctccctcgcc atgaacaagg cggggttttc    420
gccgccgagg atatgctag agctactgga aaggttggtg tctgcattgc gacttctggt    480
cctggtgcta ccaacctcgt atcaggtctt gctgacgctc tccttgattc tgtccctctt    540
gttgccatca ctggccaagt tccacgccgt atgattggca ctgatgcttt tcaggagact    600
ccaattgttg aggtgacaag gtctattact aagcataatt atttagtttt ggatgtagag    660
gatattccta gaattgttaa ggaagccttt tttttagcta attctggtag gcctggacct    720
gttttgattg atcttcctaa agatattcag cagcaattgg ttgttcctga ttgggatagg    780
ccttttaagt tgggtgggta tatgtctagg ctgccaaagt ccaagttttc gacgaatgag    840
gttggacttc ttgagcagat tgtgaggttg atgagtgagt cgaagaagcc tgtcttgtat    900
gtgggaggtg ggtgtttgaa ttctagtgag gagttgagga gatttgttga gttgacaggg    960
attccggtgg ctagtacttt gatggggttg gggtcttacc cttgtaatga tgaactgtct   1020
cttcatatgt tggggatgca cgggactgtt tatgccaatt atgcggtgga taaggcggat   1080
ttgttgcttg ctttcgggt aggtttgat gatcgtgtga ccgggaagct cgaggcgttt   1140
gctagccgtg ctaagattgt gcatattgat attgactctg ctgagattgg gaagaacaag   1200
cagccccatg tgtccatttg tgctgatgtt aaattggcat tgcggggtat gaataagatt   1260
ctggagtcta gaatagggaa gctgaatttg gatttctcca agtggagaga agaattaggt   1320
gagcagaaga aggaattccc actgagtttt aagacatttg gggatgcaat tcctccacaa   1380
tatgccattc aggtgcttga tgagttgacc aatggtaatg ctattataag tactggtgtt   1440
gggcagcacc aaatgtgggc tgcgcagcat tacaagtaca gaaaccctcg ccaatggctg   1500
acctctggtg ggttgggggc tatggggttt gggctaccag ccgccattgg agctgcagtt   1560
```

```
gctcgaccag atgcagtggt tgtcgatatt gatggggatg gcagtttat tatgaatgtt    1620 caagagttgg ctacaattag ggtggaaaat ctcccagtta agataatgct gctaaacaat    1680
caacatttag gtatggttgt ccaattggaa gataggttct ataaagctaa ccgggcacat    1740
acataccttg gaaacccttc caaatctgct gatatcttcc ctgatatgct caaattcgct    1800
gaggcatgtg atattccttc tgcccgtgtt agcaacgtgg ctgatttgag gccgccatt     1860 caaacaatgt tggatactcc agggccgtac ctgctcgatg tgattgtacc gcatcaagag    1920
catgtgttgc ctatgattcc aagtggtgcc ggtttcaagg ataccattac agagggtgat    1980
ggaagaacct cttattga                                                  1998
```

```
<210> SEQ ID NO 4
<211> LENGTH: 665
<212> TYPE: PRT
<213> ORGANISM: Beta vulgaris
<220> FEATURE:
<221> NAME/KEY: MISC_FEATURE
<222> LOCATION: (569)..(569)
<223> OTHER INFORMATION: Substitution of a Tryptophan by a Leucine

<400> SEQUENCE: 4

Met Ala Ala Thr Phe Thr Asn Pro Thr Phe Ser Pro Ser Ser Thr Pro
1               5                   10                  15

Leu Thr Lys Thr Leu Lys Ser Gln Ser Ser Ile Ser Ser Thr Leu Pro
            20                  25                  30

Phe Ser Thr Pro Pro Lys Thr Pro Thr Pro Leu Phe His Arg Pro Leu
        35                  40                  45

Gln Ile Ser Ser Ser Gln Ser His Lys Ser Ser Ala Ile Lys Thr Gln
    50                  55                  60

Thr Gln Ala Pro Ser Ser Pro Ala Ile Glu Asp Ser Ser Phe Val Ser
65                  70                  75                  80

Arg Phe Gly Pro Asp Glu Pro Arg Lys Gly Ser Asp Val Leu Val Glu
                85                  90                  95

Ala Leu Glu Arg Glu Gly Val Thr Asn Val Phe Ala Tyr Pro Gly Gly
            100                 105                 110

Ala Ser Met Glu Ile His Gln Ala Leu Thr Arg Ser Lys Thr Ile Arg
        115                 120                 125

Asn Val Leu Pro Arg His Glu Gln Gly Gly Val Phe Ala Ala Glu Gly
    130                 135                 140

Tyr Ala Arg Ala Thr Gly Lys Val Gly Val Cys Ile Ala Thr Ser Gly
145                 150                 155                 160

Pro Gly Ala Thr Asn Leu Val Ser Gly Leu Ala Asp Ala Leu Leu Asp
                165                 170                 175

Ser Val Pro Leu Val Ala Ile Thr Gly Gln Val Pro Arg Arg Met Ile
            180                 185                 190

Gly Thr Asp Ala Phe Gln Glu Thr Pro Ile Val Glu Val Thr Arg Ser
        195                 200                 205

Ile Thr Lys His Asn Tyr Leu Val Leu Asp Val Glu Asp Ile Pro Arg
    210                 215                 220

Ile Val Lys Glu Ala Phe Phe Leu Ala Asn Ser Gly Arg Pro Gly Pro
225                 230                 235                 240

Val Leu Ile Asp Leu Pro Lys Asp Ile Gln Gln Gln Leu Val Val Pro
                245                 250                 255

Asp Trp Asp Arg Pro Phe Lys Leu Gly Gly Tyr Met Ser Arg Leu Pro
            260                 265                 270
```

```
Lys Ser Lys Phe Ser Thr Asn Glu Val Gly Leu Leu Glu Gln Ile Val
            275                 280                 285

Arg Leu Met Ser Glu Ser Lys Pro Val Leu Tyr Val Gly Gly
        290                 295                 300

Cys Leu Asn Ser Ser Glu Glu Leu Arg Arg Phe Val Glu Leu Thr Gly
305                 310                 315                 320

Ile Pro Val Ala Ser Thr Leu Met Gly Leu Gly Ser Tyr Pro Cys Asn
                325                 330                 335

Asp Glu Leu Ser Leu His Met Leu Gly Met His Gly Thr Val Tyr Ala
                340                 345                 350

Asn Tyr Ala Val Asp Lys Ala Asp Leu Leu Ala Phe Gly Val Arg
                355                 360                 365

Phe Asp Asp Arg Val Thr Gly Lys Leu Glu Ala Phe Ala Ser Arg Ala
    370                 375                 380

Lys Ile Val His Ile Asp Ile Asp Ser Ala Glu Ile Gly Lys Asn Lys
385                 390                 395                 400

Gln Pro His Val Ser Ile Cys Ala Asp Val Lys Leu Ala Leu Arg Gly
                405                 410                 415

Met Asn Lys Ile Leu Glu Ser Arg Ile Gly Lys Leu Asn Leu Asp Phe
                420                 425                 430

Ser Lys Trp Arg Glu Glu Leu Gly Glu Gln Lys Lys Glu Phe Pro Leu
    435                 440                 445

Ser Phe Lys Thr Phe Gly Asp Ala Ile Pro Pro Gln Tyr Ala Ile Gln
    450                 455                 460

Val Leu Asp Glu Leu Thr Asn Gly Asn Ala Ile Ile Ser Thr Gly Val
465                 470                 475                 480

Gly Gln His Gln Met Trp Ala Ala Gln His Tyr Lys Tyr Arg Asn Pro
                485                 490                 495

Arg Gln Trp Leu Thr Ser Gly Gly Leu Gly Ala Met Gly Phe Gly Leu
    500                 505                 510

Pro Ala Ala Ile Gly Ala Ala Val Ala Arg Pro Asp Ala Val Val Val
                515                 520                 525

Asp Ile Asp Gly Asp Gly Ser Phe Ile Met Asn Val Gln Glu Leu Ala
                530                 535                 540

Thr Ile Arg Val Glu Asn Leu Pro Val Lys Ile Met Leu Leu Asn Asn
545                 550                 555                 560

Gln His Leu Gly Met Val Val Gln Leu Glu Asp Arg Phe Tyr Lys Ala
                565                 570                 575

Asn Arg Ala His Thr Tyr Leu Gly Asn Pro Ser Lys Ser Ala Asp Ile
                580                 585                 590

Phe Pro Asp Met Leu Lys Phe Ala Glu Ala Cys Asp Ile Pro Ser Ala
    595                 600                 605

Arg Val Ser Asn Val Ala Asp Leu Arg Ala Ala Ile Gln Thr Met Leu
    610                 615                 620

Asp Thr Pro Gly Pro Tyr Leu Leu Asp Val Ile Val Pro His Gln Glu
625                 630                 635                 640

His Val Leu Pro Met Ile Pro Ser Gly Ala Gly Phe Lys Asp Thr Ile
                645                 650                 655

Thr Glu Gly Asp Gly Arg Thr Ser Tyr
                660                 665

<210> SEQ ID NO 5
<211> LENGTH: 2013
```

<212> TYPE: DNA
<213> ORGANISM: Arabidopsis thaliana

<400> SEQUENCE: 5

| | | | | | |
|---|---|---|---|---|---|
| atggcggcgg | caacaacaac | aacaacaaca | tcttcttcga | tctccttctc | caccaaacca | 60 |
| tctccttcct | cctccaaatc | accattacca | atctcccaga | tctccctccc | attctcccta | 120 |
| aaccccaaca | aatcatcctc | ctcctcccgc | cgccgcggta | tcaaatccag | ctctccctcc | 180 |
| tccatctccg | ccgtgctcaa | cacaaccacc | aatgtcacaa | ccactccctc | tccaaccaaa | 240 |
| cctaccaaac | ccgaaacatt | catctcccga | ttcgctccag | atcaaccccg | caaaggcgct | 300 |
| gatatcctcg | tcgaagcttt | agaacgtcaa | ggcgtagaaa | ccgtattcgc | ttaccctgga | 360 |
| ggtgcatcaa | tggagattca | ccaagcctta | acccgctctt | cctcaatccg | taacgtcctt | 420 |
| cctcgtcacg | aacaaggagg | tgtattcgca | gcagaaggat | acgctcgatc | tcaggtaaa  | 480 |
| ccaggtatct | gtatagccac | ttcaggtccc | ggagctacaa | atctcgttag | cggattagcc | 540 |
| gatgcgttgt | tagatagtgt | tcctcttgta | gcaatcacag | acaagtccc  | tcgtcgtatg | 600 |
| attggtacag | atgcgtttca | agagactccg | attgttgagg | taacgcgttc | gattacgaag | 660 |
| cataactatc | ttgtgatgga | tgttgaagat | atccctagga | ttattgagga | agctttcttt | 720 |
| ttagctactt | ctggtagacc | tggacctgtt | ttggttgatg | ttcctaaaga | tattcaacaa | 780 |
| cagcttgcga | ttcctaattg | gaacaggct  | atgagattac | ctggttatat | gtctaggatg | 840 |
| cctaaacctc | cggaagattc | tcatttggag | cagattgtta | ggttgatttc | tgagtctaag | 900 |
| aagcctgtgt | tgtatgttgg | tggtggttgt | ttgaattcta | gcgatgaatt | gggtaggttt | 960 |
| gttgagctta | cggggatccc | tgttgcgagt | acgttgatgg | ggctgggatc | ttatccttgt | 1020 |
| gatgatgagt | tgtcgttaca | tatgcttgga | atgcatggga | cggtgtatgc | gaattacgct | 1080 |
| gtggagcata | gtgatttgtt | gttggcgttt | ggggtgaggt | ttgatgatcg | cgtcacgggt | 1140 |
| aagcttgagg | cttttgctag | tagggctaag | attgttcata | ttgatattga | ctctgctgag | 1200 |
| attgggaaga | ataagactcc | tcatgtgtct | gtgtgtggtg | atgtcaagct | ggctttgcaa | 1260 |
| gggatgaata | aggttcttga | gaaccgagct | gaggagctta | gcttgatttt | tggagtttgg | 1320 |
| aggaatgagt | tgaacgtaca | gaaacagaag | tttccgttga | gctttaagac | gtttggggaa | 1380 |
| gctattcctc | cacagtatgc | gattaaggtc | cttgatgagt | tgactgatgg | aaaagccata | 1440 |
| ataagtactg | tgtcgggca  | acatcaaatg | tgggcggcgc | agttctacaa | ttacaagaag | 1500 |
| ccaaggcagt | ggctatcatc | aggaggcctt | ggagctatgg | gttttggact | tcctgctgcc | 1560 |
| attggagcgt | ctgttgctaa | ccctgatgca | atagttgtgg | atattgacgg | agatggaagc | 1620 |
| tttataatga | atgtgcaaga | gctggccaca | atccgtgtag | agcaacttcc | agtgaagata | 1680 |
| ctcttattaa | caaccagca  | tcttggcatg | ttatgcaat  | gggaagatcg | gttctacaag | 1740 |
| gctaaccgag | ctcacacatt | tctcggggat | ccggctcagg | aggacgagat | attcccgaac | 1800 |
| atgttgctgt | ttgcagcagc | ttgcgggatt | ccagcggcga | gggtgacaaa | gaaagcagat | 1860 |
| ctccgagaag | ctattcagac | aatgctggat | acaccaggac | cttacctgtt | ggatgtgatt | 1920 |
| tgtccgcacc | aagaacatgt | gttgccgatg | atcccgagtg | gtggcacttt | caacgatgtc | 1980 |
| ataacggaag | gagatggccg | gattaaatac | tga        |            |            | 2013 |

<210> SEQ ID NO 6
<211> LENGTH: 670
<212> TYPE: PRT
<213> ORGANISM: Arabidopsis thaliana

<400> SEQUENCE: 6

```
Met Ala Ala Ala Thr Thr Thr Thr Thr Ser Ser Ser Ile Ser Phe
1               5                   10                  15

Ser Thr Lys Pro Ser Pro Ser Ser Lys Ser Pro Leu Pro Ile Ser
            20                  25                  30

Arg Phe Ser Leu Pro Phe Ser Leu Asn Pro Asn Lys Ser Ser Ser
        35                  40                  45

Ser Arg Arg Arg Gly Ile Lys Ser Ser Pro Ser Ser Ile Ser Ala
    50                  55                  60

Val Leu Asn Thr Thr Thr Asn Val Thr Thr Thr Pro Ser Pro Thr Lys
65                  70                  75                  80

Pro Thr Lys Pro Glu Thr Phe Ile Ser Arg Phe Ala Pro Asp Gln Pro
                85                  90                  95

Arg Lys Gly Ala Asp Ile Leu Val Glu Ala Leu Glu Arg Gln Gly Val
            100                 105                 110

Glu Thr Val Phe Ala Tyr Pro Gly Gly Ala Ser Met Glu Ile His Gln
            115                 120                 125

Ala Leu Thr Arg Ser Ser Ile Arg Asn Val Leu Pro Arg His Glu
        130                 135                 140

Gln Gly Gly Val Phe Ala Ala Glu Gly Tyr Ala Arg Ser Ser Gly Lys
145                 150                 155                 160

Pro Gly Ile Cys Ile Ala Thr Ser Gly Pro Gly Ala Thr Asn Leu Val
                165                 170                 175

Ser Gly Leu Ala Asp Ala Leu Leu Asp Ser Val Pro Leu Val Ala Ile
            180                 185                 190

Thr Gly Gln Val Pro Arg Arg Met Ile Gly Thr Asp Ala Phe Gln Glu
            195                 200                 205

Thr Pro Ile Val Glu Val Thr Arg Ser Ile Thr Lys His Asn Tyr Leu
210                 215                 220

Val Met Asp Val Glu Asp Ile Pro Arg Ile Ile Glu Glu Ala Phe Phe
225                 230                 235                 240

Leu Ala Thr Ser Gly Arg Pro Gly Pro Val Leu Val Asp Val Pro Lys
            245                 250                 255

Asp Ile Gln Gln Gln Leu Ala Ile Pro Asn Trp Glu Gln Ala Met Arg
            260                 265                 270

Leu Pro Gly Tyr Met Ser Arg Met Pro Lys Pro Pro Glu Asp Ser His
            275                 280                 285

Leu Glu Gln Ile Val Arg Leu Ile Ser Glu Ser Lys Lys Pro Val Leu
            290                 295                 300

Tyr Val Gly Gly Gly Cys Leu Asn Ser Ser Asp Glu Leu Gly Arg Phe
305                 310                 315                 320

Val Glu Leu Thr Gly Ile Pro Val Ala Ser Thr Leu Met Gly Leu Gly
            325                 330                 335

Ser Tyr Pro Cys Asp Asp Glu Leu Ser Leu His Met Leu Gly Met His
            340                 345                 350

Gly Thr Val Tyr Ala Asn Tyr Ala Val Glu His Ser Asp Leu Leu Leu
            355                 360                 365

Ala Phe Gly Val Arg Phe Asp Asp Arg Val Thr Gly Lys Leu Glu Ala
370                 375                 380

Phe Ala Ser Arg Ala Lys Ile Val His Ile Asp Ile Asp Ser Ala Glu
385                 390                 395                 400

Ile Gly Lys Asn Lys Thr Pro His Val Ser Val Cys Gly Asp Val Lys
            405                 410                 415
```

-continued

```
Leu Ala Leu Gln Gly Met Asn Lys Val Leu Glu Asn Arg Ala Glu Glu
            420                 425                 430
Leu Lys Leu Asp Phe Gly Val Trp Arg Asn Glu Leu Asn Val Gln Lys
        435                 440                 445
Gln Lys Phe Pro Leu Ser Phe Lys Thr Phe Gly Glu Ala Ile Pro Pro
    450                 455                 460
Gln Tyr Ala Ile Lys Val Leu Asp Glu Leu Thr Asp Gly Lys Ala Ile
465                 470                 475                 480
Ile Ser Thr Gly Val Gly Gln His Gln Met Trp Ala Ala Gln Phe Tyr
                485                 490                 495
Asn Tyr Lys Lys Pro Arg Gln Trp Leu Ser Ser Gly Gly Leu Gly Ala
            500                 505                 510
Met Gly Phe Gly Leu Pro Ala Ala Ile Gly Ala Ser Val Ala Asn Pro
        515                 520                 525
Asp Ala Ile Val Val Asp Ile Asp Gly Asp Gly Ser Phe Ile Met Asn
    530                 535                 540
Val Gln Glu Leu Ala Thr Ile Arg Val Glu Asn Leu Pro Val Lys Val
545                 550                 555                 560
Leu Leu Leu Asn Asn Gln His Leu Gly Met Val Met Gln Trp Glu Asp
                565                 570                 575
Arg Phe Tyr Lys Ala Asn Arg Ala His Thr Phe Leu Gly Asp Pro Ala
            580                 585                 590
Gln Glu Asp Glu Ile Phe Pro Asn Met Leu Leu Phe Ala Ala Ala Cys
        595                 600                 605
Gly Ile Pro Ala Ala Arg Val Thr Lys Lys Ala Asp Leu Arg Glu Ala
    610                 615                 620
Ile Gln Thr Met Leu Asp Thr Pro Gly Pro Tyr Leu Leu Asp Val Ile
625                 630                 635                 640
Cys Pro His Gln Glu His Val Leu Pro Met Ile Pro Asn Gly Gly Thr
                645                 650                 655
Phe Asn Asp Val Ile Thr Glu Gly Asp Gly Arg Ile Lys Tyr
            660                 665                 670
```